US010857020B2

(12) United States Patent
Okumura et al.

(10) Patent No.: US 10,857,020 B2
(45) Date of Patent: Dec. 8, 2020

(54) GASTROINTESTINAL TRACK CONSTRICTING METHOD

(71) Applicant: OLYMPUS CORPORATION, Tokyo (JP)

(72) Inventors: Takuya Okumura, Tokyo (JP); Shunsuke Motosugi, Tokyo (JP); Yoshie Aikawa, Tokyo (JP); Hiroyuki Morishita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 463 days.

(21) Appl. No.: 15/704,198

(22) Filed: Sep. 14, 2017

(65) Prior Publication Data

US 2019/0076283 A1    Mar. 14, 2019

(51) Int. Cl.
*A61B 1/273*    (2006.01)
*A61F 5/00*    (2006.01)
(Continued)

(52) U.S. Cl.
CPC ............ *A61F 5/0069* (2013.01); *A61B 1/273* (2013.01); *A61B 17/00234* (2013.01);
(Continued)

(58) Field of Classification Search
CPC ......... A61F 5/0069; A61B 2017/00269; A61B 2017/00818; A61B 2017/00827;
(Continued)

(56) References Cited

U.S. PATENT DOCUMENTS 5,645,560 A    7/1997    Crocker et al.
5,843,116 A    12/1998    Crocker et al.
(Continued)

FOREIGN PATENT DOCUMENTS

EP    2 298 250 A1    3/2011
EP    3 141 192 A1    3/2017
(Continued)

OTHER PUBLICATIONS

Office Action dated Sep. 9, 2019 received in U.S. Appl. No. 15/942,617.
(Continued)

*Primary Examiner* — William H Matthews
(74) *Attorney, Agent, or Firm* — Scully, Scott, Murphy & Presser, P.C.

(57) ABSTRACT

A gastrointestinal tract constricting method according to the present invention aims to constrict the gastrointestinal tract by contracting a desired region of the gastrointestinal tract by a simple and low-invasive procedure. The method includes forming spreading blocks while observing the gastrointestinal tract with an endoscope inserted into the gastrointestinal tract, the spreading blocks being formed at a position between a mucosa layer and a muscle layer and on both sides of a target region, which is to be damaged by a substance, in a circumferential direction of the gastrointestinal tract so that the spreading blocks block spreading of the substance in the circumferential direction of the gastrointestinal tract to prevent spreading of the substance to an outer side of the target region, and supplying the substance to a mucosal surface of the target region or to the position between the mucosa layer and the muscle layer after formation of the spreading blocks.

5 Claims, 16 Drawing Sheets

(51) Int. Cl.
*A61B 17/00* (2006.01)
*A61B 18/14* (2006.01)
*A61M 25/00* (2006.01)
*A61B 18/08* (2006.01)
*A61B 18/00* (2006.01)
*A61B 90/00* (2016.01)

(52) U.S. Cl.
CPC ........ *A61B 18/082* (2013.01); *A61B 18/1477* (2013.01); *A61F 5/0089* (2013.01); *A61M 25/0084* (2013.01); *A61B 18/1492* (2013.01); *A61B 90/04* (2016.02); *A61B 2017/00827* (2013.01); *A61B 2018/00488* (2013.01); *A61B 2018/00494* (2013.01); *A61B 2018/00595* (2013.01); *A61B 2018/00982* (2013.01); *A61B 2018/1475* (2013.01); *A61F 5/0079* (2013.01); *A61M 2210/105* (2013.01); *A61M 2210/1053* (2013.01)

(58) Field of Classification Search
CPC ........... A61B 2018/00488; A61B 2018/00494; A61B 1/273; A61B 17/00234; A61B 90/04; A61M 2210/1042; A61M 2210/105–1067
See application file for complete search history.

(56) References Cited

U.S. PATENT DOCUMENTS

| | | | |
|---|---|---|---|
| 6,027,486 A | 2/2000 | Crocker et al. | |
| 6,098,629 A | 8/2000 | Johnson et al. | |
| 6,338,345 B1 | 1/2002 | Johnson et al. | |
| 6,401,718 B1 | 6/2002 | Johnson et al. | |
| 6,488,653 B1 | 12/2002 | Lombardo | |
| 6,500,174 B1 | 12/2002 | Maguire et al. | |
| 6,544,226 B1 | 4/2003 | Gaiser et al. | |
| 6,575,896 B2 | 6/2003 | Silverman et al. | |
| 7,185,657 B1 | 3/2007 | Johnson et al. | |
| 2002/0148475 A1 | 10/2002 | Johnson et al. | |
| 2002/0198521 A1 | 12/2002 | Maguire | |
| 2003/0183962 A1 | 10/2003 | Buiser et al. | |
| 2003/0233150 A1 | 12/2003 | Bourne et al. | |
| 2003/0236535 A1 | 12/2003 | Onuki et al. | |
| 2004/0087936 A1 | 5/2004 | Stern et al. | |
| 2005/0096673 A1 | 5/2005 | Stack et al. | |
| 2005/0247320 A1 | 11/2005 | Stack et al. | |
| 2006/0247610 A1 | 11/2006 | Lanphere et al. | |
| 2007/0060932 A1 | 3/2007 | Stack et al. | |
| 2007/0135822 A1 | 6/2007 | Onuki et al. | |
| 2007/0260112 A1 | 11/2007 | Rahmani | |
| 2007/0260178 A1 | 11/2007 | Skerven et al. | |
| 2007/0276432 A1 | 11/2007 | Stack et al. | |
| 2008/0015523 A1 | 1/2008 | Baker et al. | |
| 2008/0065122 A1 | 3/2008 | Stack et al. | |
| 2009/0018602 A1 | 1/2009 | Mitelberg et al. | |
| 2009/0240105 A1 | 9/2009 | Smit et al. | |
| 2010/0168512 A1 | 7/2010 | Rahmani | |
| 2010/0174306 A1 | 7/2010 | Mitelberg et al. | |
| 2010/0217151 A1 | 8/2010 | Gostout et al. | |
| 2010/0241146 A1 | 9/2010 | Stack et al. | |
| 2011/0038938 A1 | 2/2011 | Ison et al. | |
| 2011/0257622 A1 | 10/2011 | Salahieh et al. | |
| 2012/0095395 A1 | 4/2012 | Haery | |
| 2012/0226300 A1 | 9/2012 | Mitelberg et al. | |
| 2012/0226302 A1 | 9/2012 | Mitelberg et al. | |
| 2013/0012863 A1 | 1/2013 | Stack et al. | |
| 2013/0197554 A1 | 8/2013 | Skerven et al. | |
| 2013/0345670 A1 | 12/2013 | Rajagopalan et al. | |
| 2014/0010847 A1 | 1/2014 | Lin | |
| 2014/0121585 A1 | 5/2014 | Baker et al. | |
| 2014/0249465 A1 | 9/2014 | Stack et al. | |
| 2015/0025313 A1 | 1/2015 | Baker et al. | |
| 2015/0032087 A1 | 1/2015 | Shibata et al. | |
| 2015/0157358 A1 | 6/2015 | Mitelberg et al. | |
| 2015/0352334 A1 | 12/2015 | Haery | |
| 2015/0374352 A1 | 12/2015 | Inoue | |
| 2016/0213890 A1 | 7/2016 | Kaufman et al. | |
| 2016/0262867 A1 | 9/2016 | Baker et al. | |
| 2016/0296675 A1 | 10/2016 | Longo et al. | |
| 2016/0310200 A1 | 10/2016 | Wang | |
| 2017/0035595 A1 | 2/2017 | Stack et al. | |
| 2018/0015264 A1 | 1/2018 | Wang et al. | |
| 2018/0296806 A1 | 10/2018 | Haery | |
| 2019/0038881 A1 | 2/2019 | Wang et al. | |
| 2019/0076283 A1 | 3/2019 | Okumura et al. | |
| 2019/0269493 A1* | 9/2019 | Okumura ................ A61F 2/04 |
| 2019/0269494 A1* | 9/2019 | Okumura ............... A61B 90/04 |
| 2019/0298476 A1* | 10/2019 | Okumura ............. A61K 31/728 |

FOREIGN PATENT DOCUMENTS

| | | |
|---|---|---|
| JP | 2000-509304 A | 7/2000 |
| JP | 2002-538932 A | 11/2002 |
| JP | 2002-540838 A | 12/2002 |
| JP | 2003-507096 A | 2/2003 |
| JP | 2003-526460 A | 9/2003 |
| JP | 2004-000601 A | 1/2004 |
| JP | 2005-521476 A | 7/2005 |
| JP | 2007-508053 A | 4/2007 |
| JP | 2008-526461 A | 7/2008 |
| JP | 2009-533150 A | 9/2009 |
| JP | 2009-536083 A | 10/2009 |
| JP | 2010-533036 A | 10/2010 |
| JP | 2014-508580 A | 4/2014 |
| JP | 2014-521390 A | 8/2014 |
| JP | 2014-171629 A | 9/2014 |
| JP | 2014-188205 A | 10/2014 |
| JP | 2015-023904 A | 2/2015 |
| JP | 2015-033634 A | 2/2015 |
| JP | 2015-066144 A | 4/2015 |
| JP | 2016-032523 A | 3/2016 |
| JP | 2016-154927 A | 9/2016 |
| JP | 2016-185296 A | 10/2016 |
| JP | 2017-533036 A | 11/2017 |
| JP | 2018-504209 A | 2/2018 |
| WO | 1997/40877 A1 | 11/1997 |
| WO | 2000/56237 A2 | 9/2000 |
| WO | 00/59398 A1 | 10/2000 |
| WO | 2001/012255 A1 | 2/2001 |
| WO | 01/68015 A1 | 9/2001 |
| WO | 03/082359 A1 | 10/2003 |
| WO | 2005/037152 A1 | 4/2005 |
| WO | 2006/078672 A1 | 7/2006 |
| WO | 2007/120727 A1 | 10/2007 |
| WO | 2007/131112 A2 | 11/2007 |
| WO | 2009/009274 A2 | 1/2009 |
| WO | 2012/054387 A2 | 4/2012 |
| WO | 2012/099974 A2 | 7/2012 |
| WO | 2012/162114 A1 | 11/2012 |
| WO | 2015/016162 A1 | 2/2015 |
| WO | 2016/070032 A1 | 5/2016 |
| WO | 2016/118923 A1 | 7/2016 |
| WO | 2016/158290 A1 | 10/2016 |

OTHER PUBLICATIONS

Office Action dated Aug. 3, 2020 received in U.S. Appl. No. 15/942,617.

Office Action dated Mar. 16, 2020 received in U.S. Appl. No. 15/942,617.

* cited by examiner

GASTROINTESTINAL TRACK CONSTRICTING METHOD

TECHNICAL FIELD

The present invention relates to a gastrointestinal tract constricting method.

BACKGROUND ART

Heretofore, known methods for treating gastroesophageal reflux disease, which is a benign disorder caused by degradation of the function of the cardiac sphincter at the entrance of the stomach, include oral administration of a proton pump inhibitor (PPI) that decreases the amount of gastric acid, the Nissen fundoplication technique (fundoplication technique) that involves wrapping a part of the stomach around the esophagus, the LINX technique that involves squeezing the esophagus with a magnet band or rubber band, the TIF technique that involves pulling the cardiac part under peroral endoscopy and stapling the cardiac part in the pulled state to form a valve, etc.

In addition, the methods described in, for example, PTL 1 and PTL 2 are other known methods for treating gastroesophageal reflux disease. The method described in PTL 1 involves removing tissue from the surface of the gastrointestinal tract, such as the esophagus, the stomach, or the like, and re-constructing the body passageway by utilizing the healing response. In PTL 2, the gastrointestinal tract is constricted by deliberately causing scars to form by incising at least one of a mucosa layer and a submucosal layer in the gastroesophageal junction or stomach.

CITATION LIST

Patent Literature

{PTL 1} Japanese Translation of PCT International Application, Publication No. 2009-536083
{PTL 2} US Patent Application No. 2015/0374352

SUMMARY OF INVENTION

An aspect of the present invention provides a gastrointestinal tract constricting method, the method comprising forming spreading blocks while observing the gastrointestinal tract with an endoscope inserted into the gastrointestinal tract, the spreading blocks being formed at a position between a mucosa layer and a muscle layer and on both sides of a target region, which is to be damaged by a substance, in a circumferential direction of the gastrointestinal tract so that the spreading blocks block spreading of the substance in the circumferential direction of the gastrointestinal tract to prevent spreading of the substance to an outer side of the target region, and supplying the substance to a mucosal surface of the target region or to the position between the mucosa layer and the muscle layer after formation of the spreading blocks.

DESCRIPTION OF EMBODIMENTS

First Embodiment

A gastrointestinal tract constricting method according to a first embodiment of the present invention will now be described with reference to the drawings.

Figure 1:
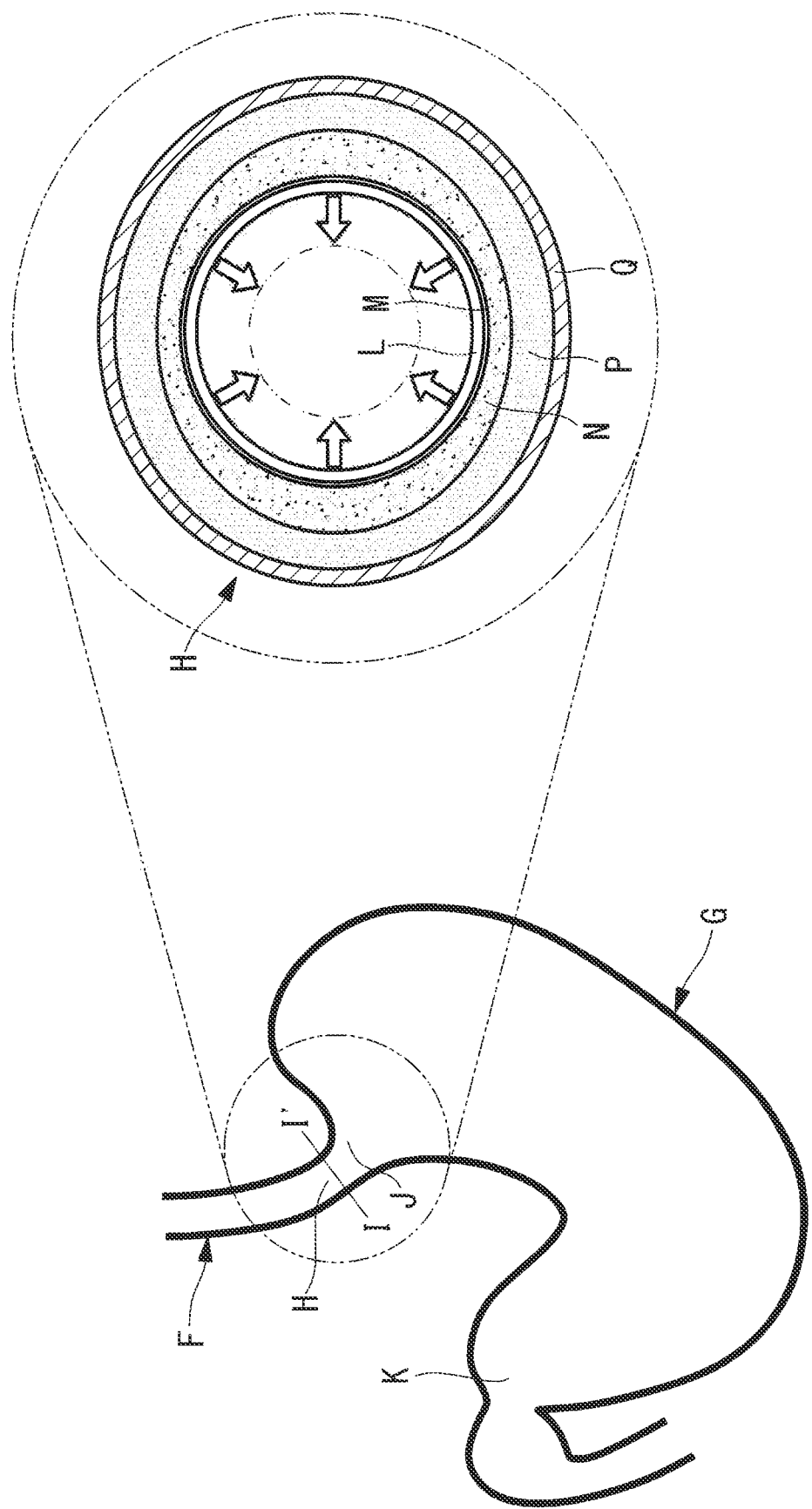
FIG. 1 includes a plan view of a periphery of the gastroesophageal junction to which a gastrointestinal tract constricting method according to a first embodiment of the present invention is applied, and a transversal sectional view of the gastroesophageal junction.

The case described as an example in this embodiment is the case in which the gastrointestinal tract constricting method is applied to the treatment of gastroesophageal reflux disease, and, as illustrated in FIG. 1, a part of a region that extends from the vicinity (lower part of the esophagus) of the gastroesophageal junction (gastrointestinal tract) H, where the esophagus F connects to the stomach G, to the cardiac part is constricted. In FIG. 1, reference sign J denotes the cardiac part constituting the entrance of the stomach G, reference sign K denotes the pyloric part constituting the endmost part of the stomach G, reference sign L denotes a mucosa layer, reference sign M denotes a mucosa basal layer, reference sign N denotes a submucosal layer, reference sign P denotes a muscle layer, and reference sign Q denotes a serosa.

Figure 2:
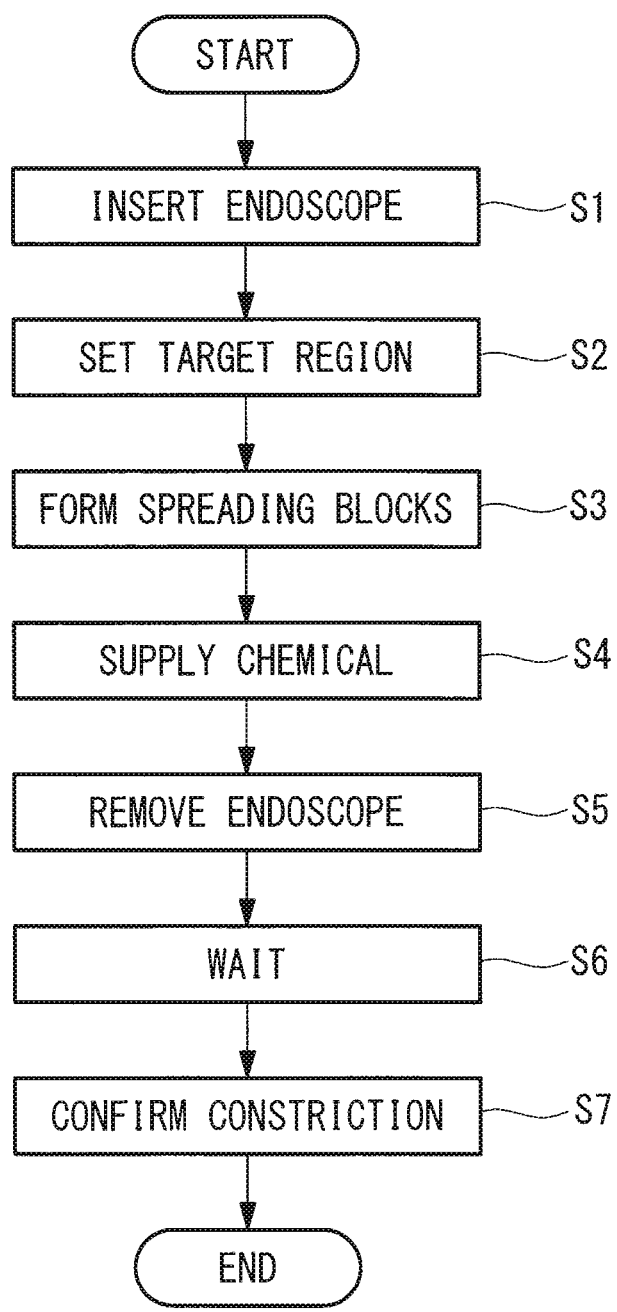
FIG. 2 is a flowchart illustrating the gastrointestinal tract constricting method according to the first embodiment of the present invention.

As illustrated in the flowchart of FIG. 2, the gastrointestinal tract constricting method includes an inserting step S1 of inserting an endoscope into the gastrointestinal tract so as to deliver the distal end portion of the endoscope to a position at which the gastroesophageal junction H can be observed from the inside of the gastrointestinal tract; an identifying step S2 of identifying, under endoscopic observation, a target region where the tissue (mucosa basal layer M) located between the mucosa layer L and the muscle layer P in a part of a region extending from the vicinity (lower part of the esophagus) of the gastroesophageal junction H to the cardiac part J is to be damaged by ethanol (substance); a forming step S3 of forming spreading blocks that block spreading of ethanol to the outer side of the target region; a supplying step S4 of supplying ethanol to the target region after the forming step S3; an endoscope removing step S5 of removing an endoscope 1 from the gastrointestinal tract to the outside of the body; a waiting step S6 of waiting until the gastroesophageal junction H is constricted; and a constriction confirming step S7 of confirming constriction of the gastroesophageal junction H. Note that spreading described in the present application means extending in the circumferential direction of the gastrointestinal tract.

Figure 3:
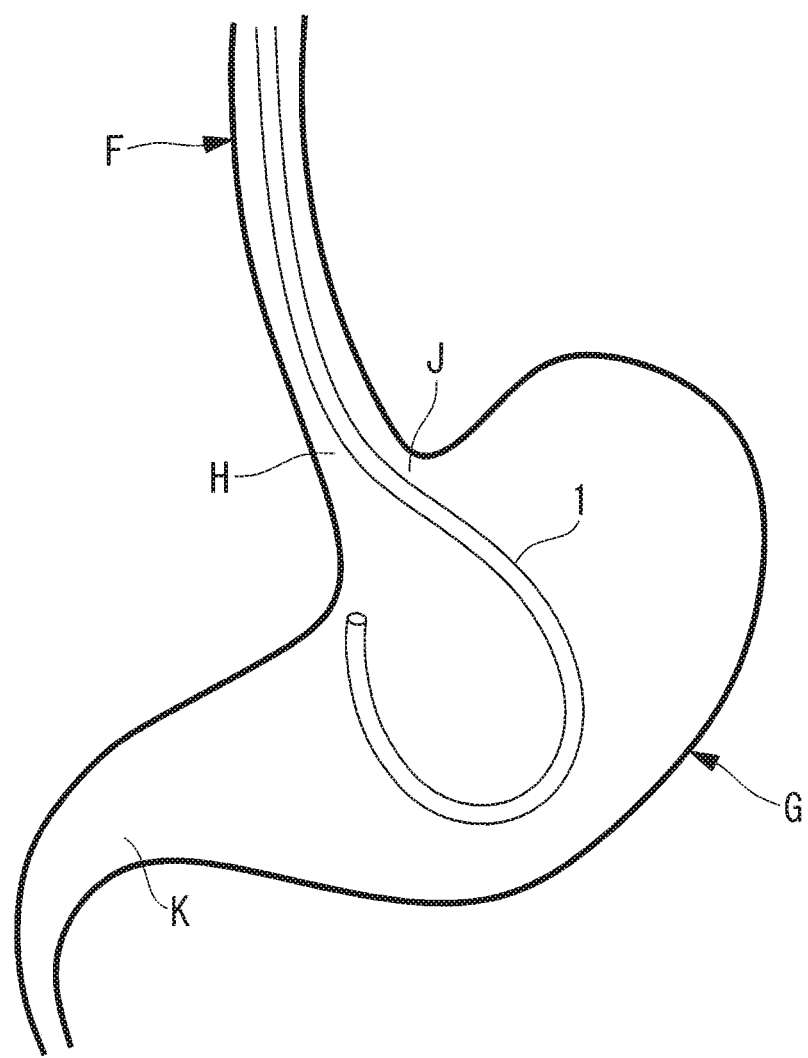
FIG. 3 is a longitudinal sectional view showing how an endoscope is inserted into the stomach illustrated in FIG. 1.

As illustrated in FIG. 3, in the inserting step S1, the endoscope 1 is inserted via the mouth of a subject into the stomach G through the esophagus F, the distal end of the endoscope 1 is bent inside the stomach G, and the endoscope 1 is arranged to face the cardiac part J and the gastroesophageal junction H so that the distal end of the endoscope 1 looks up into the esophagus F from the stomach G.

Figure 4:
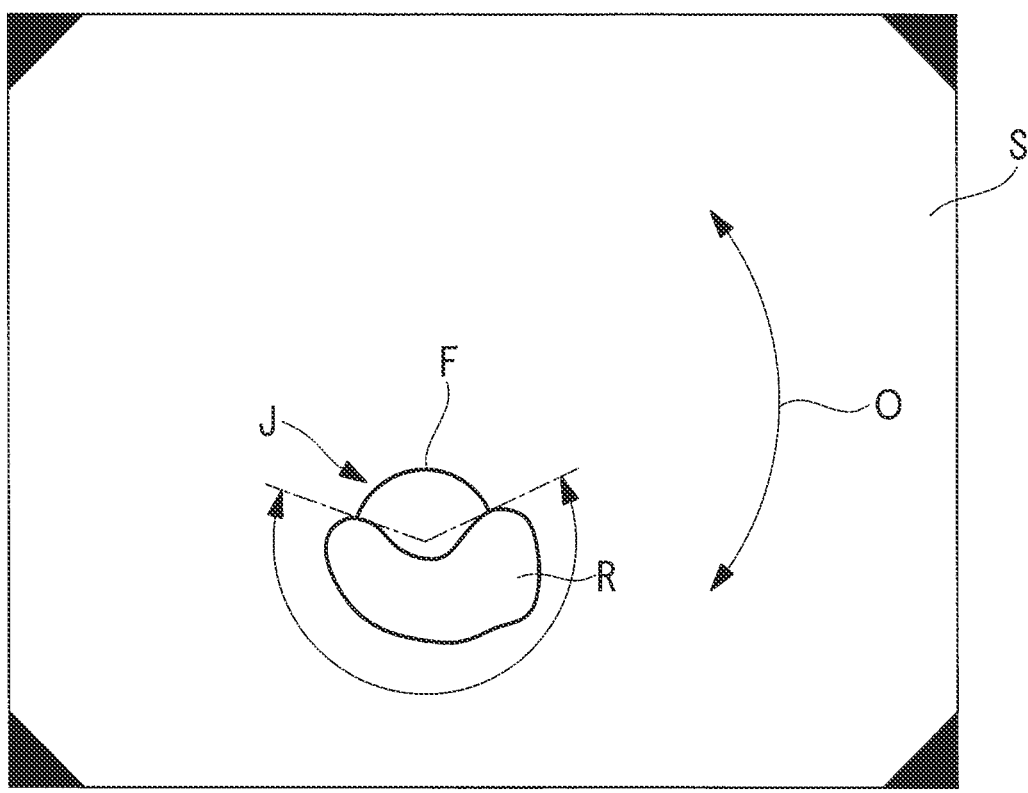
FIG. 4 is an endoscopic image of the gastroesophageal junction illustrated in FIG. 1 and a mucosal surface in a target region, as viewed from the inside of the stomach.

In the identifying step S2, as illustrated in FIG. 4, after the mucosal surface of the relaxed cardiac part J is observed with the endoscope 1, the range of a target region R on the mucosal surface is identified. In FIG. 4, reference sign S denotes the gastric wall, and the arrow indicated by reference sign O indicates the circumferential direction of the gastrointestinal tract. The same applies to FIGS. 7, 13, and 18.

Figure 5:
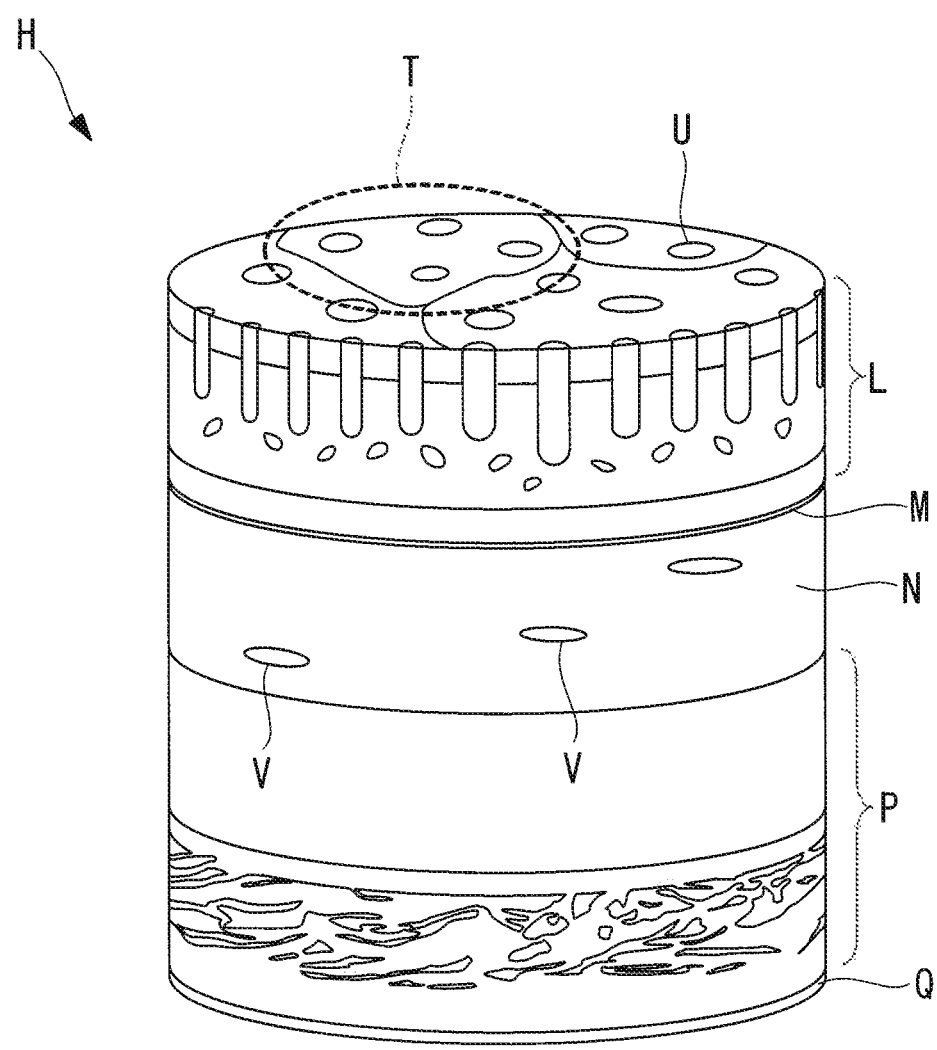
FIG. 5 is a longitudinal sectional view illustrating the structure of the gastric wall illustrated in FIG. 1.

In the supplying step S4 described below, in the range coincident with the thus-identified target region R, the mucosa basal layer M (refer to FIGS. 1 and 5), which is the lowermost layer of the mucosa layer L, in a part of the region extending from the vicinity (lower part of the esophagus) of the gastroesophageal junction H to the cardiac part J is damaged. By damaging the mucosa basal layer M in this target region R, constriction occurs in the part of the region extending from the vicinity (lower part of the esophagus) of the gastroesophageal junction H to the cardiac part J. Preferably, the range of the target region R is appropriately determined in advance so that the lumen after the constriction has a desired inner diameter. In FIG. 5, reference sign T denotes the gastric area, reference sign U denotes the gastric foveola, and V denotes a blood vessel.

Note that, the target region R is a part of the region extending from the vicinity (lower part of the esophagus) of the gastroesophageal junction H to the cardiac part J and does not cover the entire circumference so as to prevent excessive constriction. For example, as illustrated in FIG. 6, the target region R is preferably a range that extends from the lesser curvature side to the gastric fundus side and occupies 60% to 80% of the entire circumference.

Figure 6:
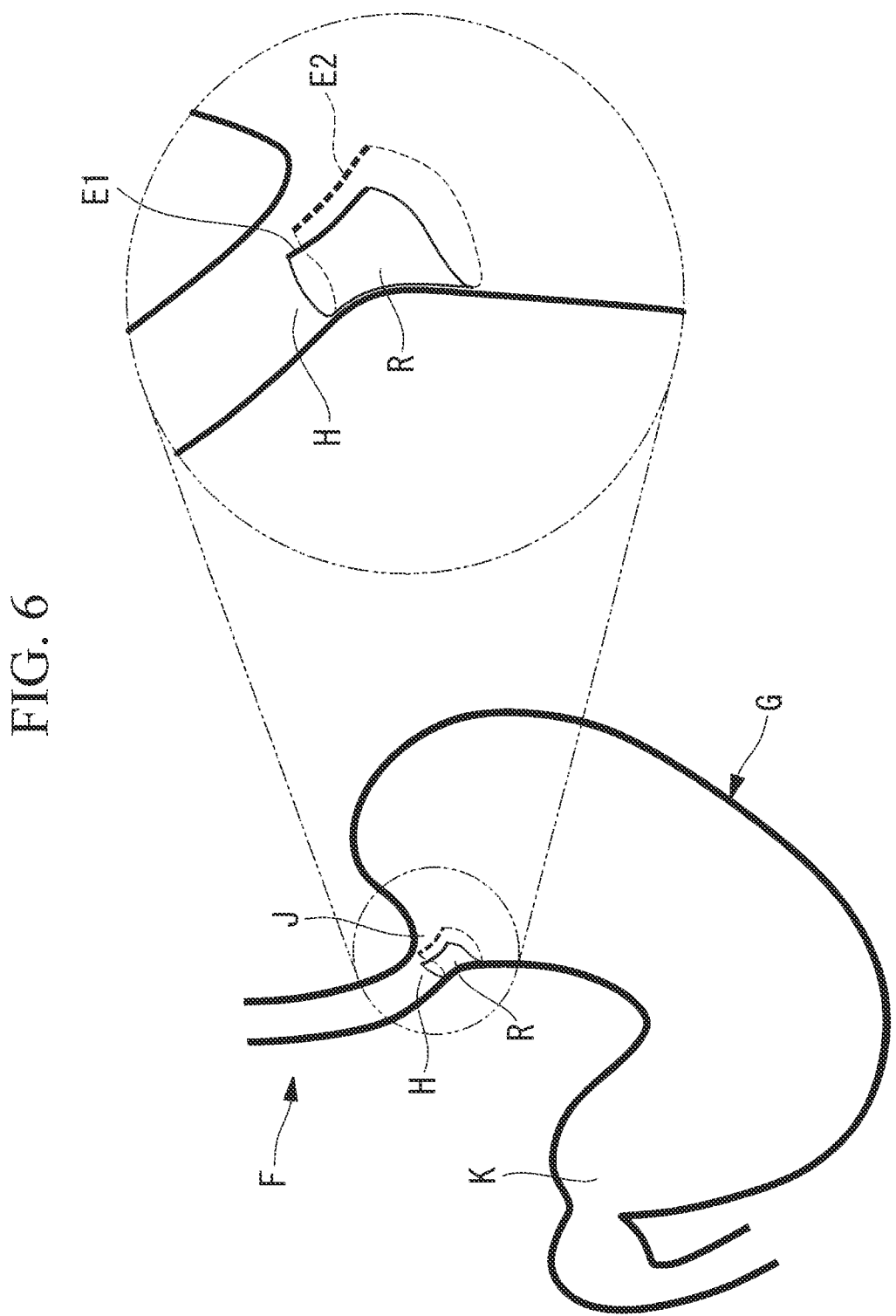
FIG. 6 is a plan view illustrating the position of the target region in the gastroesophageal junction.
Figure 7:
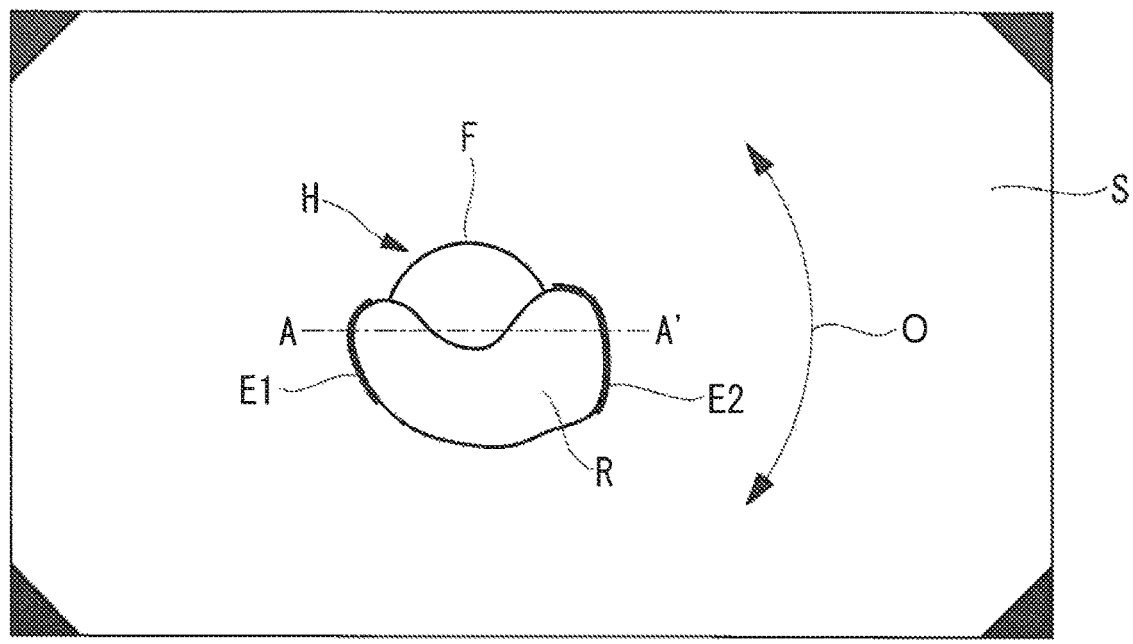
FIG. 7 is an endoscopic image of the target region illustrated in FIG. 4 and spreading blocks on the two sides of the target region.
Figure 8:
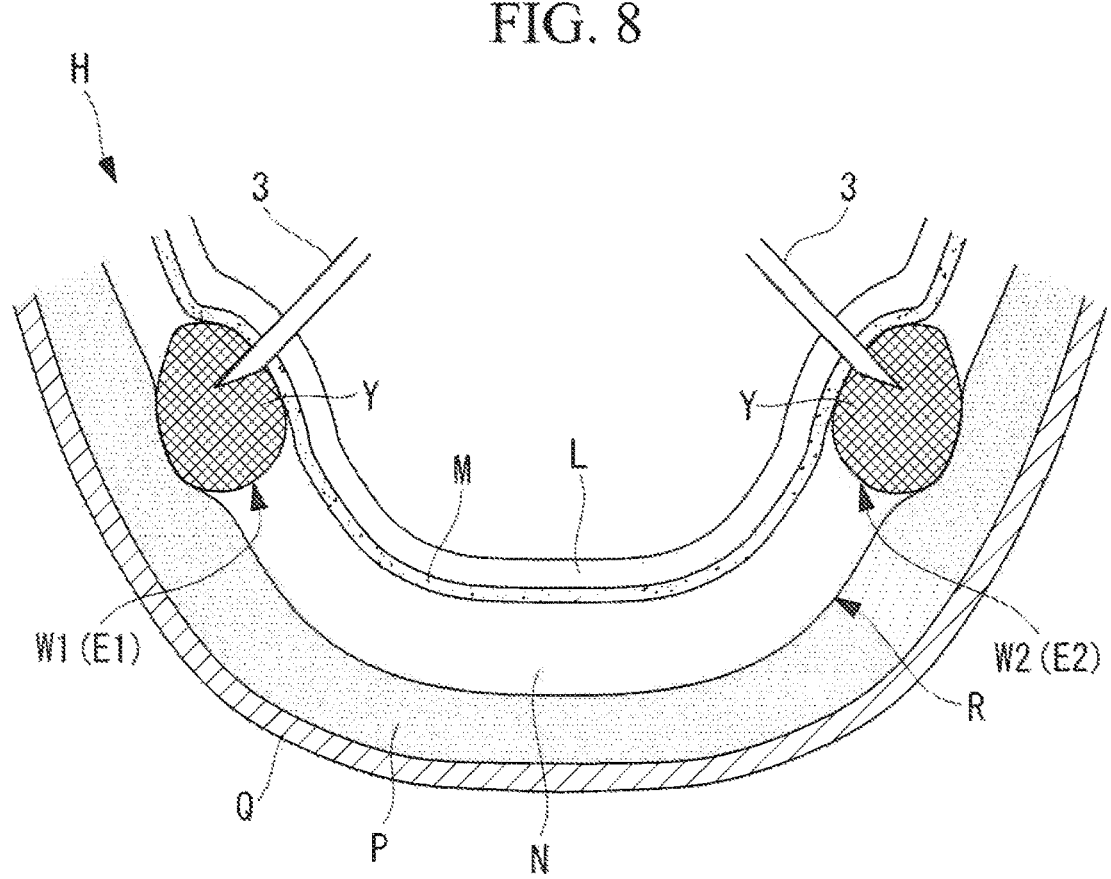
FIG. 8 is a sectional view taken along A-A' in FIG. 7 illustrating how spreading blocks are formed by injecting a sodium hyaluronate solution at the two sides of the target region.

In the forming step S3, an spreading inhibitor is used to form spreading blocks W1 and W2 in the submucosal layer (position between the mucosa layer L and the muscle layer P) N in a first adjacent region E1 and a second adjacent region E2 on both sides of the target region R in the circumferential direction of the gastroesophageal junction H, as illustrated in FIGS. 6 and 7, so that the spreading blocks W1 and W2 are provided along the target region R, as illustrated in FIG. 8. As the spreading inhibitor, for example, a sodium hyaluronate solution is used as a liquid that is immiscible with ethanol due to substance polarity or has a higher viscosity than ethanol. The substance polarity referred to here is the electric bias present within the molecule.

In this forming step S3, specifically, a treatment tool equipped with an injection needle (not illustrated) is first inserted into a forceps channel in the endoscope 1 inserted in the gastrointestinal tract, and then a syringe (not illustrated) filled with a sodium hyaluronate solution is attached to the injection-needle-equipped treatment tool. Next, in the forming step S3, as illustrated in FIGS. 7 and 8, an injection needle 3 of the injection-needle-equipped treatment tool sequentially punctures the first adjacent region E1, which is adjacent to one end of the target region R in the circumferential direction and extends along the target region R, and the second adjacent region E2, which is adjacent to the other end of the target region R and extends along the target region R, so as to inject the sodium hyaluronate solution Y into the submucosal layer N in the adjacent regions E1 and E2.

In the forming step S3, this operation is repeated several times so as to form a first spreading block (spreading block) W1 and a second spreading block (spreading block) W2 on the both sides of the target region R in the circumferential direction of the gastroesophageal junction H. The sodium hyaluronate solution Y can remain at the injected position in the submucosal layer N due to its high viscosity.

Figure 12:
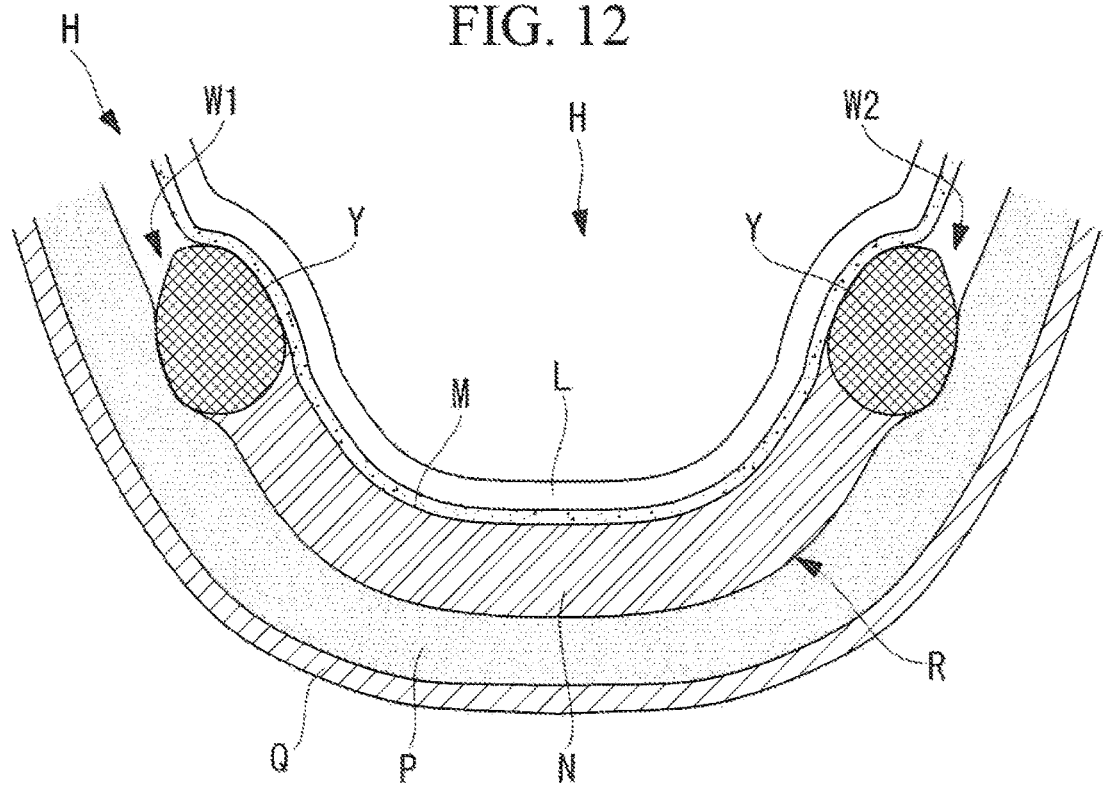
FIG. 12 is a transversal sectional view illustrating the periphery of the target region illustrated in FIG. 11 after injection of ethanol.

Moreover, because the sodium hyaluronate solution Y is injected into the submucosal layer N in the adjacent regions E1 and E2, spaces (for example, the tissue spaces) in the submucosal layer N in the adjacent regions E1 and E2 are filled with the sodium hyaluronate solution Y. In other words, the first spreading block W1 and the second spreading block W2 composed of the sodium hyaluronate solution Y are formed. As a result, as illustrated in FIG. 12, in the supplying step S4 described below, ethanol Z injected into the target region R can remain within the range of the target region R while being prevented from spreading beyond what is necessary in the circumferential direction of the gastroesophageal junction H through the space (for example, the tissue space) in the submucosal layer N. In other words, while preventing the ethanol Z from spreading over the entire circumference of the gastroesophageal junction H, the mucosa basal layer M can be damaged within the desired target region R range.

Figure 9:
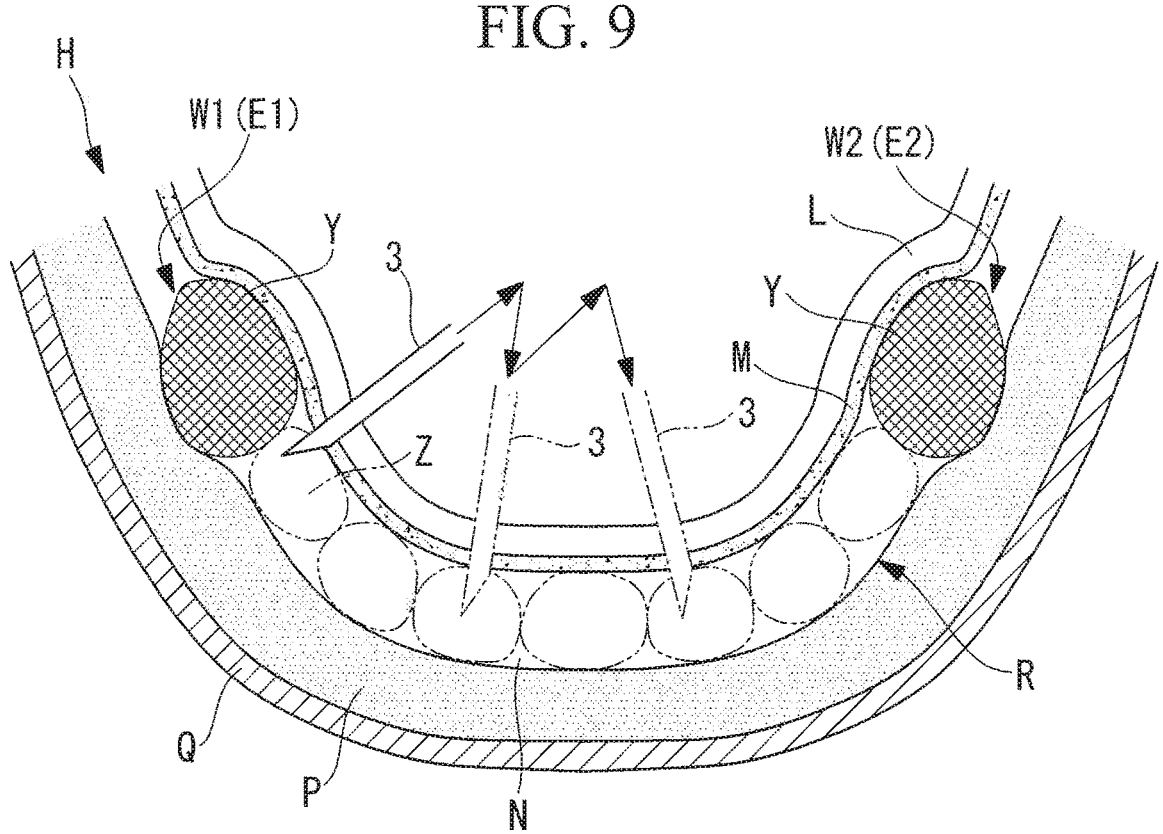
FIG. 9 is a transversal sectional view showing how ethanol is injected into the target region illustrated in FIG. 8.

In the supplying step S4, a syringe (not illustrated) filled with ethanol is attached to the treatment tool equipped with an injection needle, so as to replace the syringe filled with the sodium hyaluronate solution Y. Then, in the supplying step S4, as illustrated in FIG. 9, the injection needle 3 of the injection-needle-equipped treatment tool punctures the target region R so as to inject the ethanol Z into the submucosal layer (the position between the mucosa layer L and the muscle layer P) N, and this operation is repeated several times while changing the position within the target region R.

The effects of the gastrointestinal tract constricting method having such features will now be described.

In order to constrict a part of the region extending from the vicinity (lower part of the esophagus) of the gastroesophageal junction H to the cardiac part J of the subject by the gastrointestinal tract constricting method according to this embodiment, first, as illustrated in FIG. 3, the endoscope 1 is inserted into the gastrointestinal tract through the mouth of the subject, and the distal end of the endoscope 1 is bent inside the stomach G so as to face the cardiac part J and the gastroesophageal junction H (inserting step S1).

Next, as illustrated in FIG. 4, while observing the region that extends from the vicinity (lower part of the esophagus) of the gastroesophageal junction H to the cardiac part J with the endoscope 1, the target region R is identified within the region that extends from the vicinity (lower part of the esophagus) of the gastroesophageal junction H to the cardiac part J (identifying step S2).

Once the target region R is identified, the injection-needle-equipped treatment tool is inserted into the forceps channel of the endoscope 1, and a syringe filled with the sodium hyaluronate solution Y is attached to the injection-needle-equipped treatment tool.

Next, as illustrated in FIG. 7, injection needle 3 of the injection-needle-equipped treatment tool sequentially punctures the first adjacent region E1 and the second adjacent region E2 that are respectively adjacent to the two end portions of the target region R in the circumferential direction so as to inject the sodium hyaluronate solution Y into the submucosal layer N in the adjacent regions E1 and E2. This operation is repeated several times so that, as illustrated in FIG. 8, the first spreading block W1 and the second spreading block W2 formed by filling with the sodium hyaluronate solution Y are formed at a position between the mucosa layer L and the muscle layer P and on the both sides of the target region R in the circumferential direction of the gastroesophageal junction H (forming step S3). In other words, in the state in which the first spreading block W1 and the second spreading block W2 are formed, the target region R lies between the first spreading block W1 and the second spreading block W2.

Once the spreading blocks W1 and W2 are formed, a syringe filled with the ethanol Z is attached to the injection-needle-equipped treatment tool, and, as illustrated in FIG. 9, the injection needle 3 of the injection-needle-equipped treatment tool punctures the target region R so as to inject the ethanol Z into the submucosal layer N. This operation is repeated several times while changing the position within the target region R (supplying step S4). The ethanol Z reaches the mucosa basal layer M and damages the mucosa basal layer M before it is absorbed in the body. In other words, the ethanol Z is absorbed in the body after it damages the mucosa basal layer M. The sodium hyaluronate solution Y is absorbed in the body more slowly than the ethanol Z is. Thus, until the ethanol Z is absorbed in the body, the state in which the first spreading block W1 and the second spreading block W2 are formed is maintained.

In the supplying step S4, the ethanol Z is repeatedly injected into the submucosal layer N while changing the position within the target region R until the ethanol Z injected into the submucosal layer N reaches and contacts the sodium hyaluronate solution Y injected into the submucosal layer N. The spread range of the ethanol Z injected into the submucosal layer N can be confirmed by the position of the bulge in the mucosal surface.

After the supplying step S4, whether the state in which the ethanol Z injected into the submucosal layer N reaches and contacts the sodium hyaluronate solution Y injected into the submucosal layer N is created is confirmed, and then the endoscope 1 is removed out of the body from the gastrointestinal tract (endoscope removing step S5).

After the endoscope 1 is taken out of the body from the gastrointestinal tract, the operation thereof is waited until the part of the region extending from the vicinity (lower part of the esophagus) of the gastroesophageal junction H to the cardiac part J is constricted by the constrictive effect of the tissue around the target region R undergoing the process of forming scars as the damaged tissue heals (waiting step S6).

After waiting of the operation until the part of the region extending from the vicinity (lower part of the esophagus) of the gastroesophageal junction H to the cardiac part J is constricted, the endoscope 1 is again inserted into the gastrointestinal tract so as to confirm that the part of the region extending from the vicinity (lower part of the esophagus) of the gastroesophageal junction H to the cardiac part J is constricted (constriction confirming step S7). If needed, after the sodium hyaluronate solution Y is injected into the submucosal layer N as described in the forming step S3, the ethanol Z may be additionally injected into the submucosal layer N as described in the supplying step S4.

Figure 10:
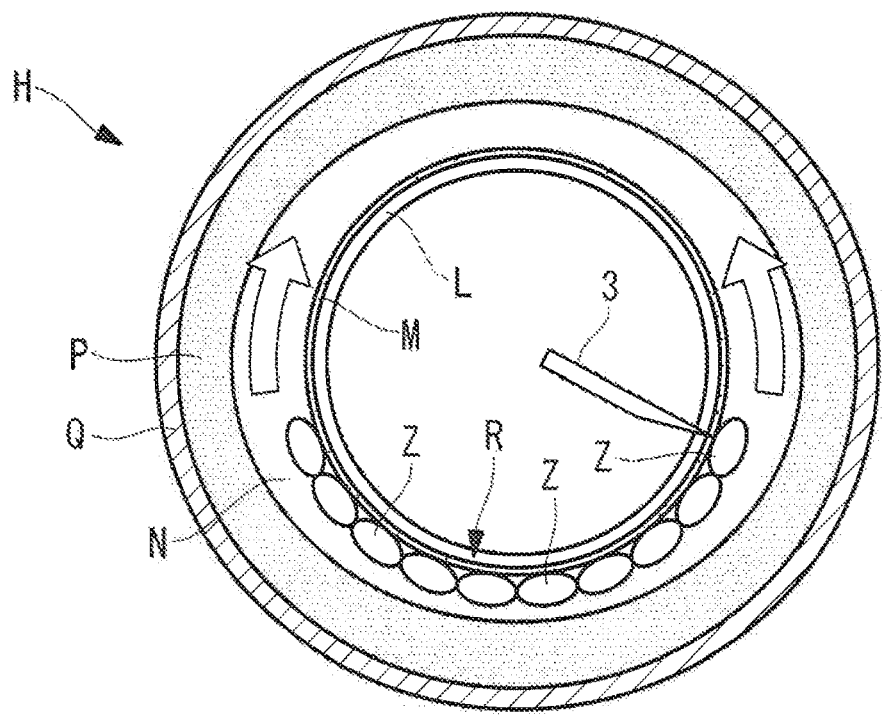
FIG. 10 is a transversal sectional view of the gastroesophageal junction illustrating how ethanol spreads in the circumferential direction if spreading blocks are not formed on the two sides of the target region.

In such a case, for example, if the spreading blocks W1 and W2 on the both sides of the target region R in the circumferential direction of the gastroesophageal junction H are absent, as illustrated in FIG. 10, it is possible that the ethanol Z injected into the target region R will spread in the circumferential direction (direction along the surface of the wall of the gastrointestinal tract) of the gastroesophageal junction H.

Figure 11:
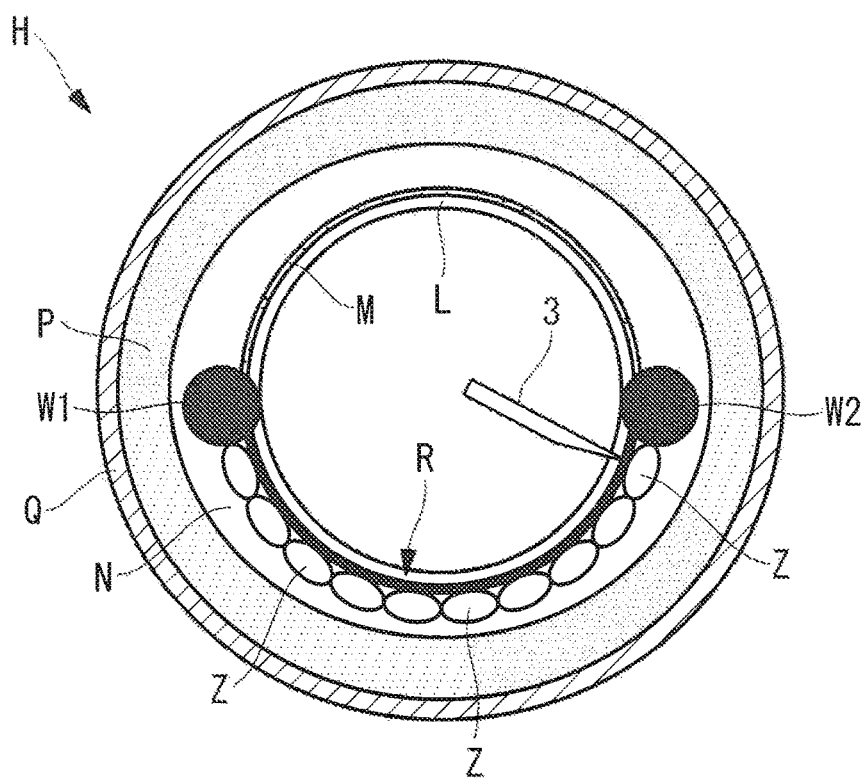
FIG. 11 is a transversal sectional view of the gastroesophageal junction illustrating how the spreading blocks formed on the two sides of the target region block spreading of ethanol in the circumferential direction.

In contrast, as illustrated in FIG. 11, when the spreading blocks W1 and W2 are formed on the both sides of the target region R in the circumferential direction of the gastroesophageal junction H, the ethanol Z injected into the target region R is blocked by the spreading blocks W1 and W2, and thus, the ethanol Z is prevented from spreading beyond what is necessary in the circumferential direction of the gastroesophageal junction H. In other words, the ethanol Z is prevented from spreading around the entire circumference of the gastroesophageal junction H.

As a result, as illustrated in FIG. 12, the ethanol Z can damage the mucosa basal layer M within the desired target region R range in the gastroesophageal junction H. Thus, by using the constrictive effect of the tissue around the target region R undergoing the process of forming scars as the damaged tissue heals, the part of the region extending from the vicinity (lower part of the esophagus) of the gastroesophageal junction H to the cardiac part J is constricted, and thus gastric acid reflux can be suppressed.

As described above, according to the gastrointestinal tract constricting method of this embodiment, the tissue located between the mucosa layer L and the muscle layer P in the target region R of the gastroesophageal junction H is damaged by the ethanol Z; thus, compared to the case in which the tissue is damaged by incising the gastroesophageal junction H or excising the tissue of the gastroesophageal junction H, the invasiveness is low and the procedure is simple.

Moreover, because the spreading blocks W1 and W2 are formed on the both sides of the target region R in the circumferential direction of the gastroesophageal junction H before injection of the ethanol Z, damage to the tissue over a wide range, caused by the ethanol Z supplied to the target region R spreading beyond what is necessary in the circumferential direction of the gastroesophageal junction H, is prevented, and thus excessive constriction of the gastroesophageal junction H can be prevented. Thus, the part of the region that extends from the vicinity (lower part of the esophagus) of the gastroesophageal junction H to the cardiac part J can be constricted by constricting the desired region of the gastroesophageal junction H by a simple and low-invasive procedure.

Although ethanol Z is described as an example of the substance in this embodiment, the substance may be any substance that impairs normal functions of cells, in other words, any substance that can damage cells, and examples thereof include, in addition to ethanol Z, peptase, protease, acetylcysteine, and sodium 2-mercaptoethanesulfonate.

Although the sodium hyaluronate solution Y is described as an example of the spreading inhibitor, the spreading inhibitor may be any liquid that does not easily spread but remains at the position at which it is placed in the submucosal layer N, and examples thereof include, in addition to the sodium hyaluronate solution Y, sodium chondroitin sulfate, chitosan, poly-N-acetylglucosamine, carboxymethyl cellulose sodium, carmellose sodium, and cyanoacrylate.

Among these substances and spreading inhibitors, a combination of a substance and an spreading inhibitor that are immiscible with each other, such as a combination of the ethanol Z and the sodium hyaluronate solution Y described above, may be used.

In this embodiment, the spreading blocks W are formed by injecting the sodium hyaluronate solution Y at a position between the mucosa layer L and the muscle layer P of the gastroesophageal junction H; alternatively, an absorbent polymer may be used so that spreading of the substance in the circumferential direction of the gastroesophageal junction H is suppressed by absorption by the absorbent polymer.

In this case, for example, the absorbent polymer may be placed at positions between the mucosa layer L and the muscle layer P in two regions respectively adjacent to the two end portions of the target region R in the circumferential direction so that spreading blocks are formed on the both sides of the target region R in the circumferential direction of the gastroesophageal junction H.

Second Embodiment

A gastrointestinal tract constricting method according to a second embodiment of the present invention will now be described with reference to the drawings.

Figure 13:
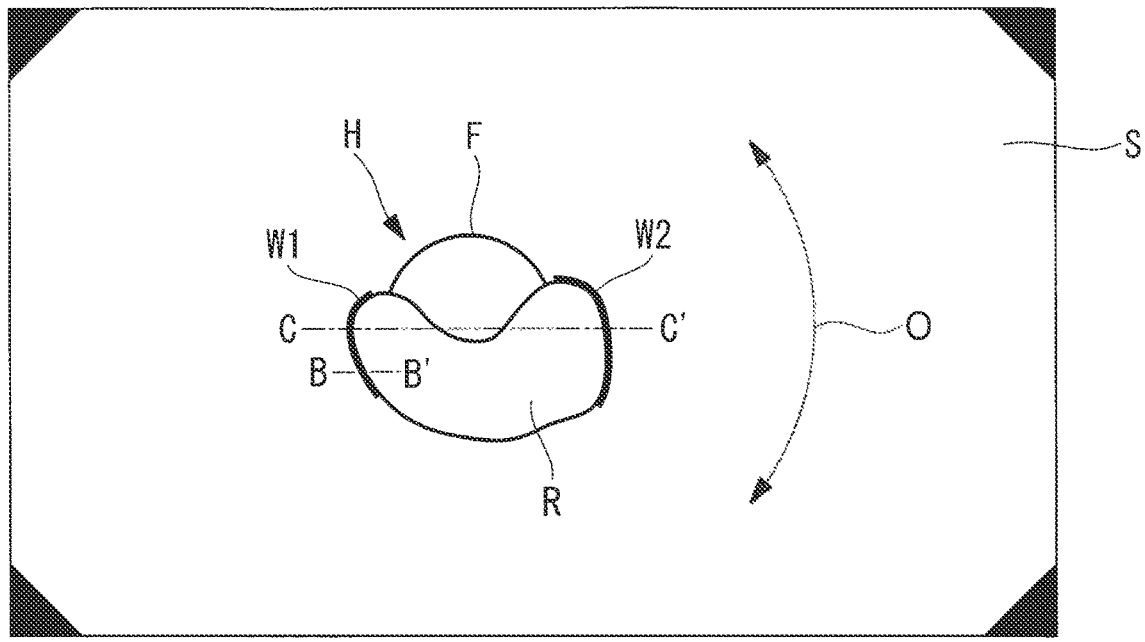
FIG. 13 is an endoscopic image of the target region and the spreading blocks on the two sides of the target region, as viewed from the inside of the stomach, when a gastrointestinal tract constricting method according to a second embodiment of the present invention is applied.
Figure 14:
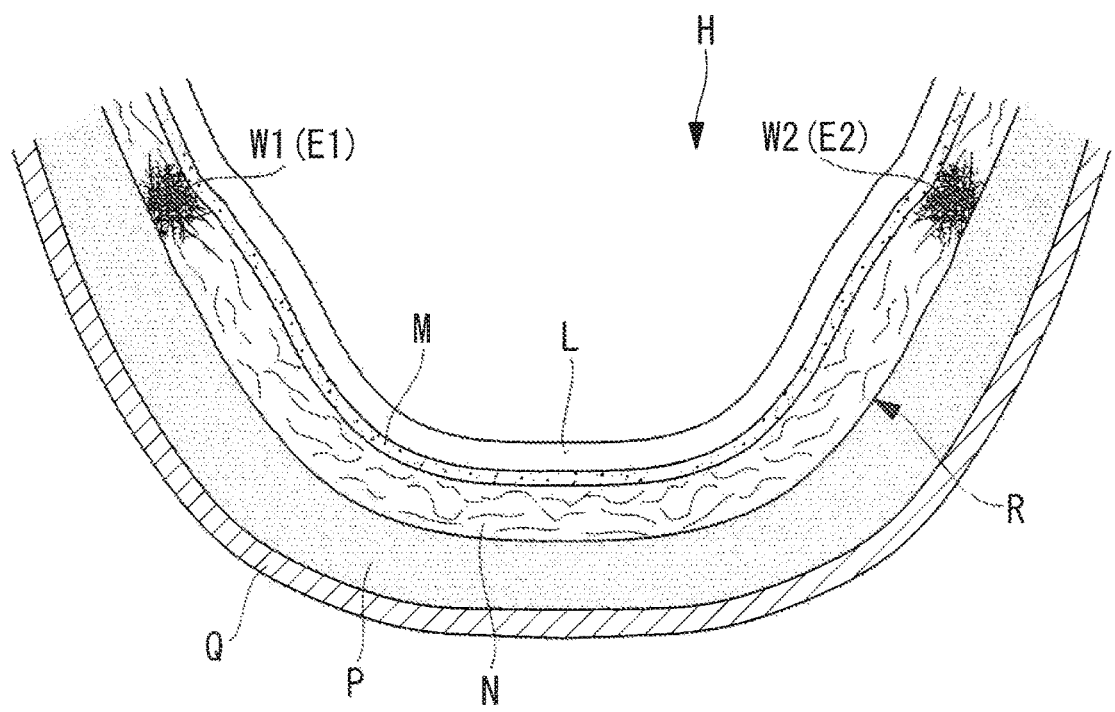
FIG. 14 is a sectional view taken along C-C' in FIG. 13, in which spreading blocks are formed.

The gastrointestinal tract constricting method according to this embodiment differs from the first embodiment in that, in the forming step S3, the submucosal layer (position between the mucosa layer L and the muscle layer P) N of the first adjacent region E1 and the second adjacent region E2 on the both sides of the target region R in the circumferential direction of the gastroesophageal junction H is cauterized, as illustrated in FIG. 13, to form the spreading blocks W1 and W2 on the two sides of the target region R, as illustrated in FIG. 14. The inserting step S1, the identifying step S2, the supplying step S4, the endoscope removing step S5, the waiting step S6, and the constriction confirming step S7 are the same as in the first embodiment.

In the description of this embodiment, the parts common to the gastrointestinal tract constricting method according to the first embodiment described above are denoted by the same reference signs, and descriptions therefor are omitted.

Figure 15:
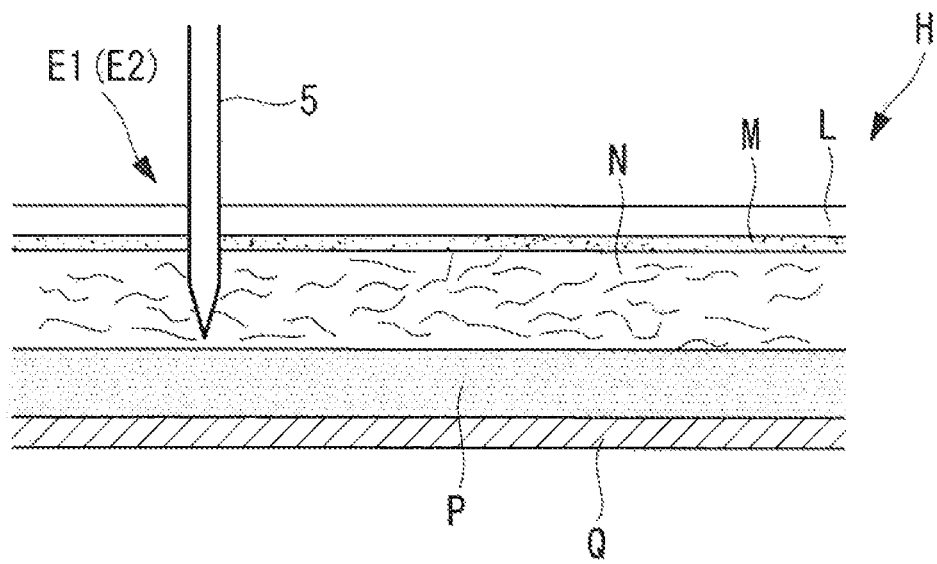
FIG. 15 is a sectional view taken along B-B' in FIG. 13, in which a needle electrode punctures a submucosal layer.
Figure 16:
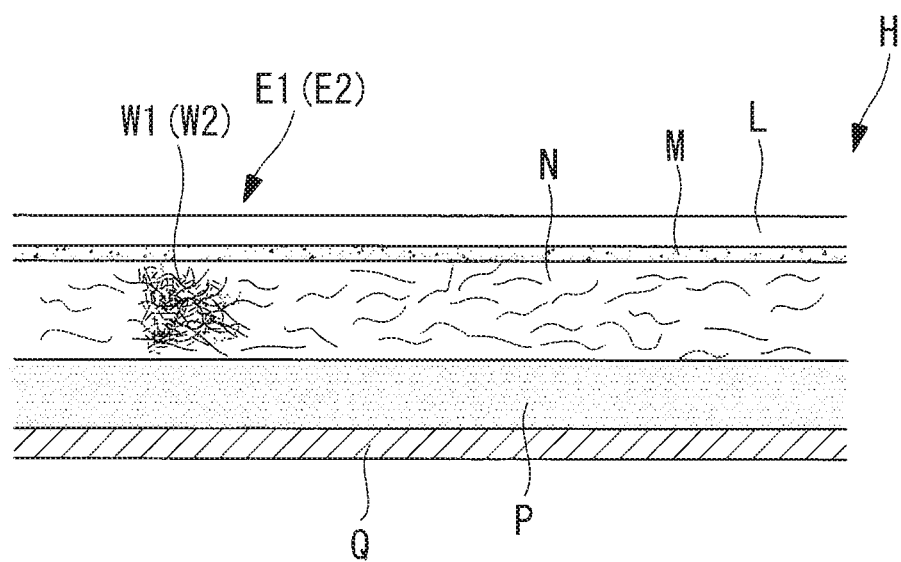
FIG. 16 is a longitudinal sectional view illustrating how the submucosal layer illustrated in FIG. 15 is cauterized by the needle electrode so as to be agglutinated and coagulated.

In the forming step S3 of this embodiment, a needle electrode-equipped treatment tool (not illustrated) is inserted into the forceps channel in the endoscope 1 inserted into the gastrointestinal tract in the inserting step S1, and, as illustrated in FIGS. 13 and 15, needle electrode 5 of the needle electrode-equipped treatment tool sequentially punctures the first adjacent region E1 and the second adjacent region E2 adjacent to the target region R identified in the identifying step S2. Next, in the forming step S3, the tissues of the submucosal layer N in the adjacent regions E1 and E2 are cauterized with the needle electrode 5, as illustrated in FIG. 16, so as to agglutinate and coagulate the tissues.

Figure 17:
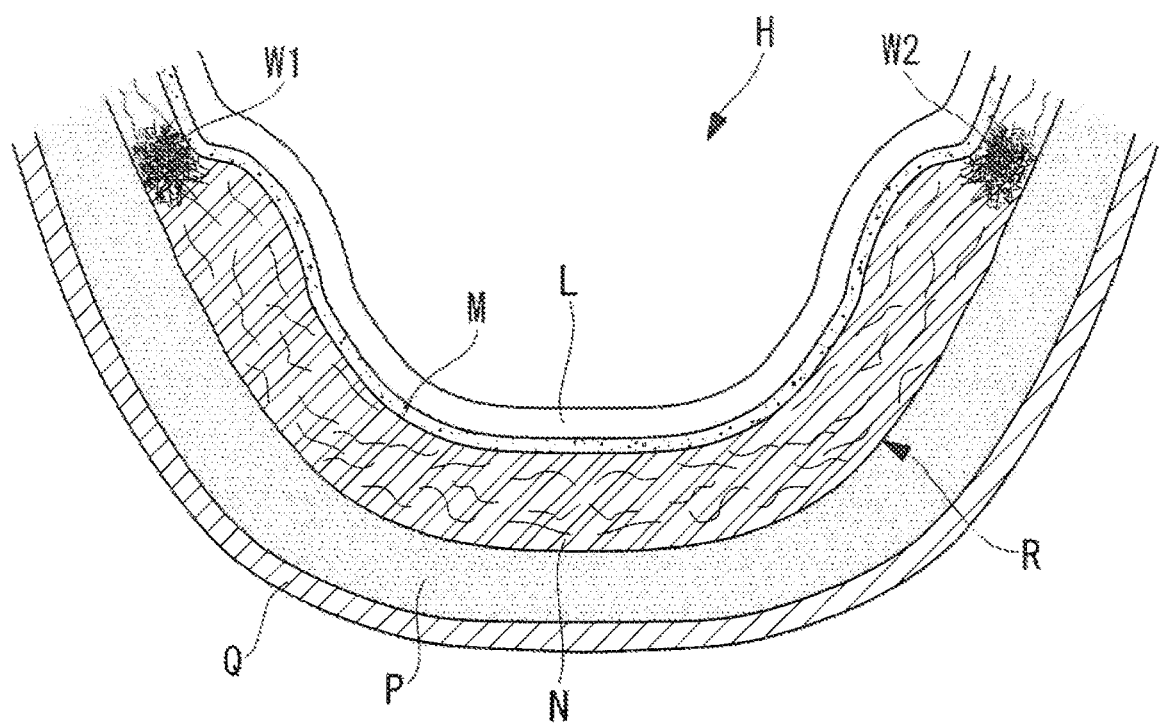
FIG. 17 is a transversal sectional view illustrating the periphery of the target region illustrated in FIG. 14 after injection of ethanol.

In the forming step S3, this operation is repeated several times so as to form the first spreading block W1 and the second spreading block W2 on the both sides of the target region R in the circumferential direction of the gastroesophageal junction H, as illustrated in FIG. 14. When the tissues of the submucosal layer N in the adjacent regions E1 and E2 are agglutinated and coagulated by cauterization, spaces (for example, the tissue spaces) in the submucosal layer N on the both sides of the target region R in the circumferential direction of the gastroesophageal junction H can be eliminated. As a result, as illustrated in FIG. 17, in the supplying step S4 described below, the ethanol Z injected into the target region R can remain within the range of the target region R while being prevented from spreading beyond what is necessary in the circumferential direction of the gastroesophageal junction H through the space (for example, the tissue space) in the submucosal layer N. In other words, while preventing the ethanol Z from spreading over the entire circumference of the gastroesophageal junction H, the mucosa basal layer M can be damaged within the desired target region R range.

According to the thus-configured gastrointestinal tract constricting method of this embodiment, the spreading blocks W1 and W2 can be easily formed on the both sides of the target region R in the circumferential direction by a simple procedure of merely cauterizing the tissues at the position between the mucosa layer L and the muscle layer P of the gastroesophageal junction H. In this embodiment, the tissues in the submucosal layer N agglutinated and coagulated by cauterization function as the spreading blocks W1 and W2. Moreover, unlike in the case of forming the spreading blocks W1 and W2 by using an spreading inhibitor such as the sodium hyaluronate solution Y, there is no need to consider the combination of the sodium hyaluronate solution Y and a substance that damages the tissue at the position between the mucosa layer L and the muscle layer P in the target region R. Thus, there is no need to pose limits on the type of substance that damages the tissue at the position between the mucosa layer L and the muscle layer P in the target region R.

Third Embodiment

A gastrointestinal tract constricting method according to a third embodiment of the present invention will now be described with reference to the drawings.

Figure 18:
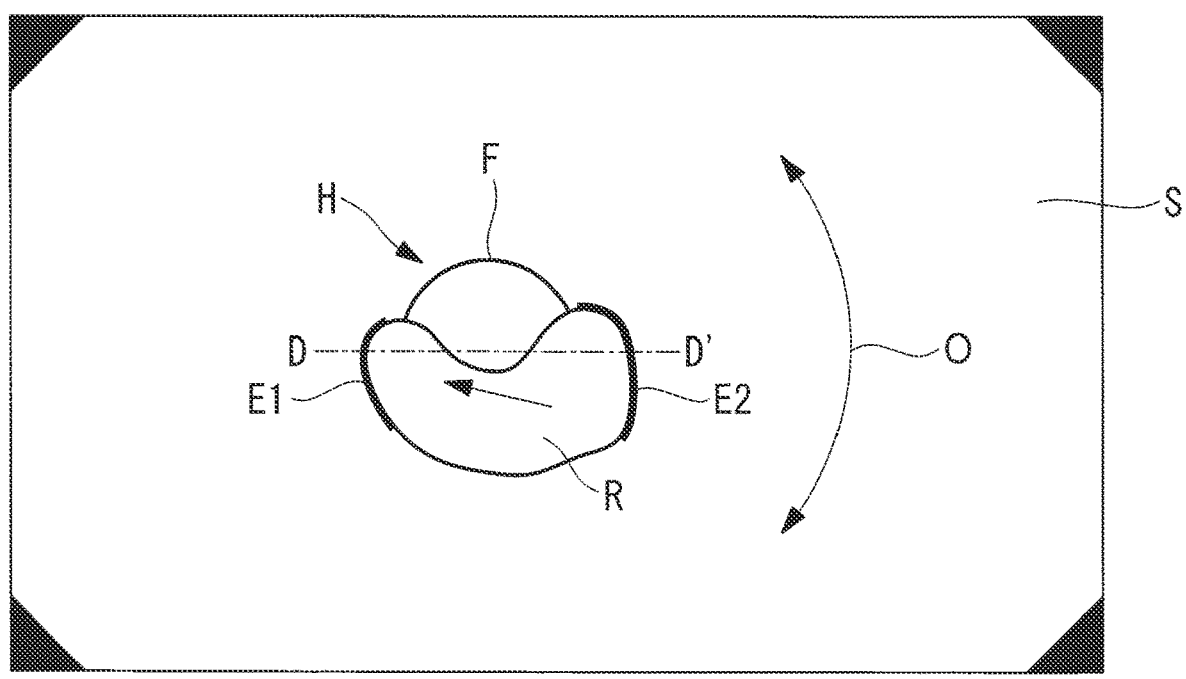
FIG. 18 is an endoscopic image of the target region and the spreading blocks on the two sides of the target region, as viewed from the inside of the stomach, when a gastrointestinal tract constricting method according to a third embodiment of the present invention is applied.
Figure 19:
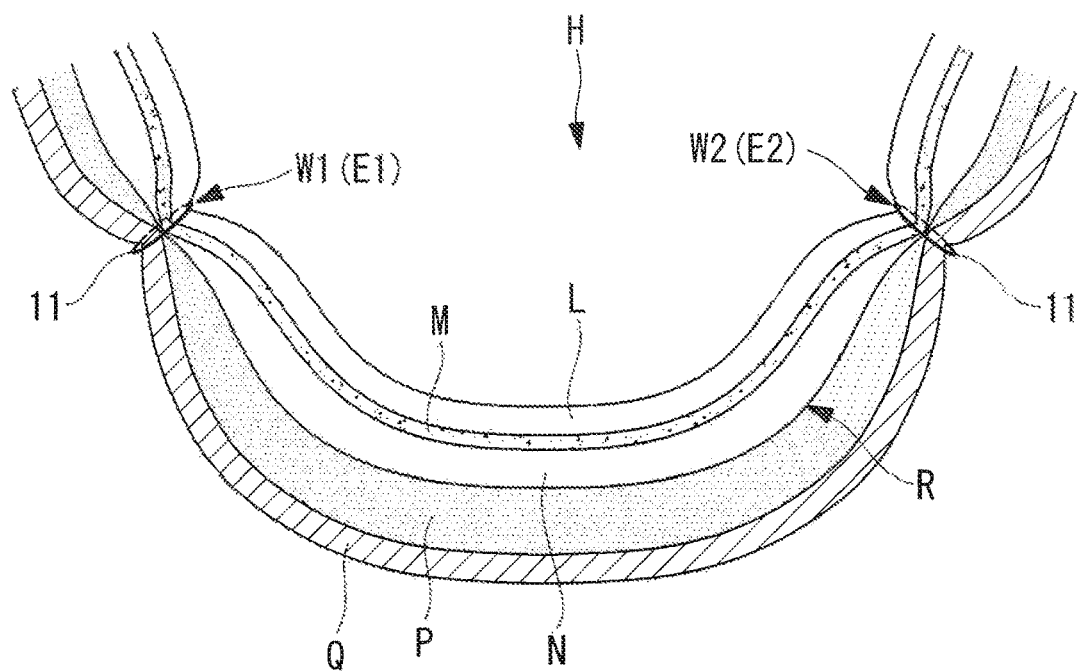
FIG. 19 is a sectional view taken along D-D' in FIG. 18, in which spreading blocks are formed.

The gastrointestinal tract constricting method according to this embodiment differs from the first embodiment in that, in the forming step S3, the submucosal layer (position between the mucosa layer L and the muscle layer P) N in the first adjacent region E1 and the second adjacent region E2 adjacent to the target region R is compressed as illustrated in FIGS. 18 and 19 to form the spreading blocks W1 and W2 on the two sides of the target region R. The identifying step S2, the supplying step S4, the endoscope removing step S5, the waiting step S6, and the constriction confirming step S7 are the same as in the first embodiment.

In the description of this embodiment, the parts common to the gastrointestinal tract constricting method according to the first embodiment described above are denoted by the same reference signs, and descriptions therefor are omitted.

Figure 20:
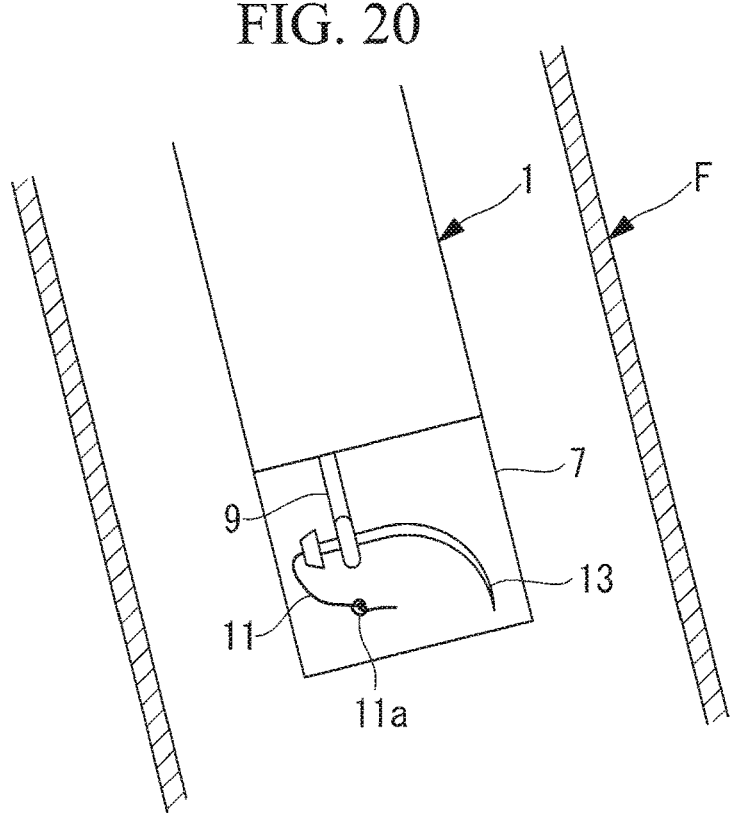
FIG. 20 is a longitudinal sectional view illustrating how the endoscope is inserted into the gastrointestinal tract while a needle-attached suture thread is grasped by grasping forceps inserted into a forceps channel in the endoscope.

In the inserting step S1, as illustrated in FIG. 20, a cap 7 is attached to the distal end of the endoscope 1, a grasping forceps 9 is inserted into the forceps channel of the endoscope 1, and a needle-attached suture thread 11 is grasped by the grasping forceps 9. In the inserting step S1, the endoscope 1 is inserted from the mouth of the subject into the gastrointestinal tract, and the distal end of the endoscope is delivered to the position at which the gastroesophageal junction H can be observed from the inside of the gastrointestinal tract. In order to prevent the needle-attached suture thread 11 from slipping-off, a knot 11a is preferably formed at an end of the needle-attached suture thread 11 in advance. The needle-attached suture thread 11 is equipped with a barb and does not become loose after suturing.

In the forming step S3, as illustrated in FIG. 18, the needle-attached suture thread 11 grasped by the grasping forceps 9 is used to suture and tuck the mucosa layer L and the serosa Q in the layered direction (thickness direction or radial direction of the gastrointestinal tract) in the first adjacent region E1 and the second adjacent region E2 adjacent to the target region R. In the forming step S3, this operation is repeated several times so that, as illustrated in FIG. 19, the tissues between the mucosa layer L and the serosa Q are in close contact with each other in the layered direction (thickness direction or radial direction of the gastrointestinal tract) at the both sides of the target region R in the circumferential direction of the gastroesophageal junction H so as to form the first spreading block W1 and the second spreading block W2 formed by eliminating the space in the submucosal layer N (for example, the tissue space). In this embodiment, the tissues in the submucosal layer N tucked by suture or the like function as the spreading blocks W1 and W2.

The effects of the gastrointestinal tract constricting method, having such features, will now be described.

In order to constrict a part of the region extending from the vicinity (lower part of the esophagus) of the gastroesophageal junction H to the cardiac part J of the subject by the gastrointestinal tract constricting method according to this embodiment, first, as illustrated in FIG. 20, the cap 7 is attached to the distal end of the endoscope 1, the grasping forceps 9 is inserted into the forceps channel of the endoscope 1, and the needle-attached suture thread 11 is grasped by the grasping forceps 9. Under such conditions, the endoscope 1 is inserted via the mouth of the subject into the gastrointestinal tract, and the distal end of the endoscope is delivered to the position at which the gastroesophageal junction H can be observed from the inside of the gastrointestinal tract (inserting step S1).

Next, while observing the region that extends from the vicinity (lower part of the esophagus) of the gastroesophageal junction to the cardiac part J with the endoscope 1, the target region R that extends from the vicinity (lower part of the esophagus) of the gastroesophageal junction H to the cardiac part J is identified (identifying step S2), and, as illustrated in FIG. 19, the spreading blocks W1 and W2 are formed by using the needle-attached suture thread 11 grasped by the grasping forceps 9 (forming step S3).

Figure 21:
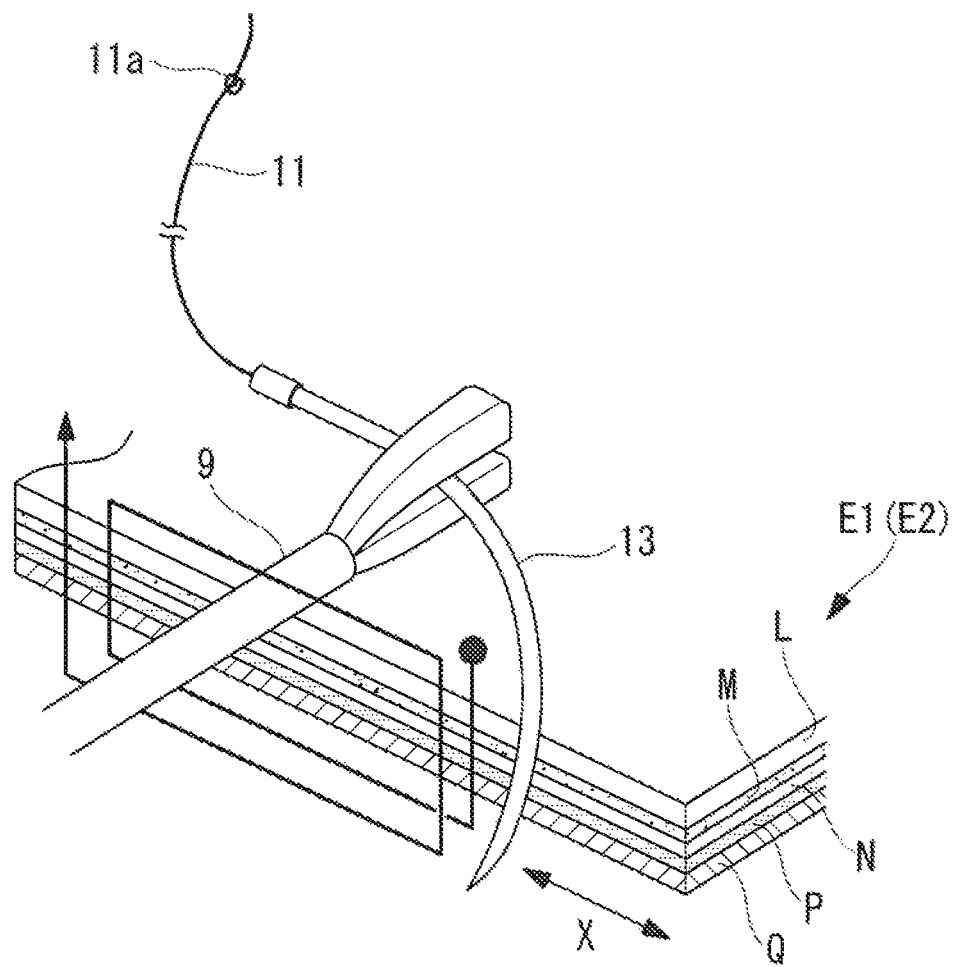
FIG. 21 illustrates how the needle of the needle-attached suture thread grasped by the grasping forceps punctures the tissue from the surface of the mucosa layer toward the serosa side.
Figure 22:
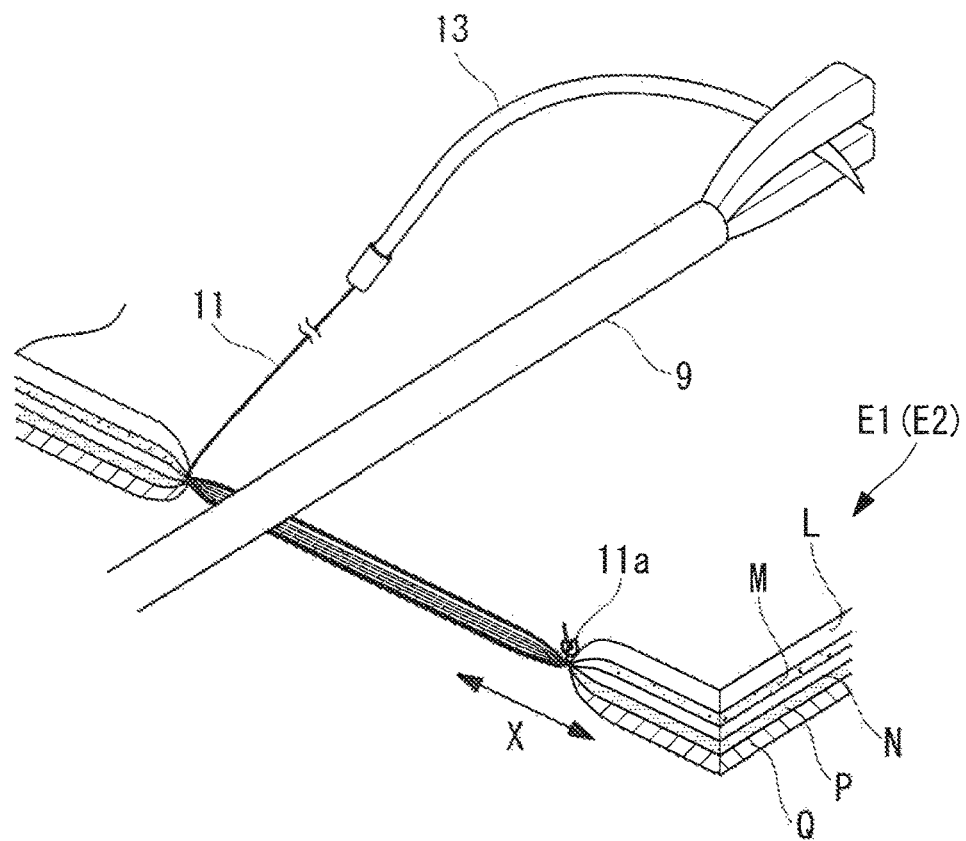
FIG. 22 is a diagram illustrating how the tissues between a mucosa layer and a serosa in the first adjacent region and the second adjacent region, which extend along the longitudinal direction of the gastroesophageal junction and lie on the two sides of the target region in the circumferential direction, are sutured so that the tissues are in close contact with each other in a layered direction.
Figure 23:
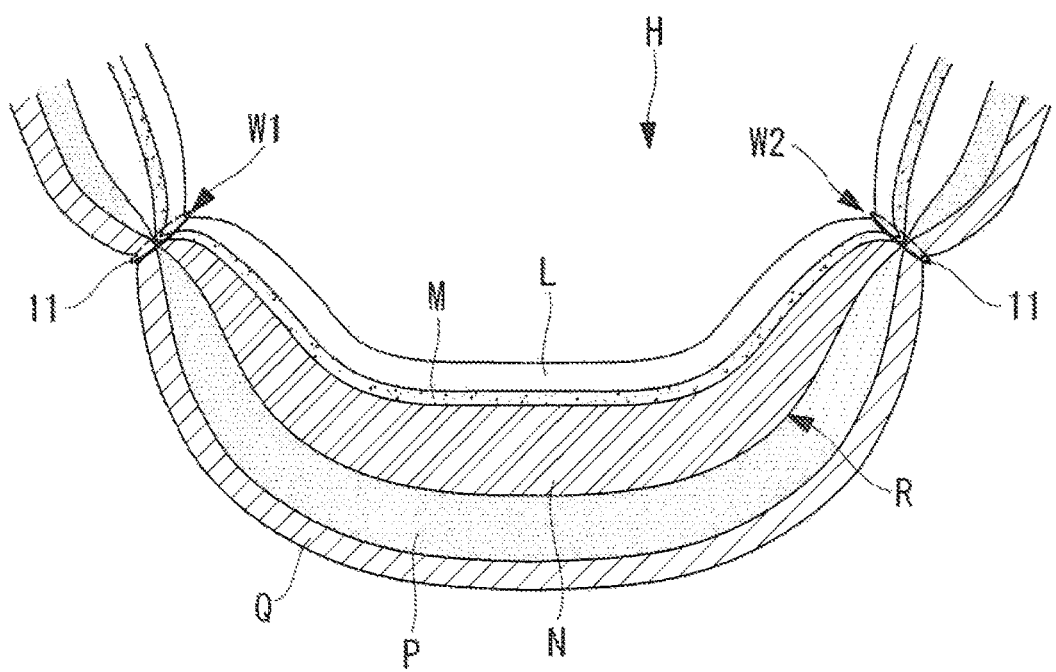
FIG. 23 is a sectional view taken along D-D' in FIG. 18 after injection of ethanol.

Specifically, first, as illustrated in FIG. 18, in the first adjacent region E1 adjacent to one end of the target region R in the circumferential direction of the esophagus, the first adjacent region E1 is sutured by using the needle-attached suture thread 11 grasped by the grasping forceps 9 by the procedure illustrated in FIG. 21, and then squeezed by pulling the suture so as to bring the tissues between the mucosa layer L and the serosa Q in the first adjacent region E1 into close contact with each other in the layered direction as illustrated in FIGS. 22 and 23. In FIGS. 21 and 22, the arrow X shows the longitudinal direction of the esophagus.

Next, as illustrated in FIG. 18, the operation illustrated in FIGS. 21 and 22 is repeated in the second adjacent region E2 adjacent to the other end of the target region R in the circumferential direction to suture the second adjacent region E2 so that the tissues between the mucosa layer L and the serosa Q in the second adjacent region E2 in the longitudinal direction of the esophagus are in close contact with each other in the layered direction, as illustrated in FIGS. 22 and 23.

As a result, as illustrated in FIG. 19, the first spreading block W1 and the second spreading block W2 are formed on the both sides of the target region R in the circumferential direction of the gastroesophageal junction H by performing suturing in the direction that brings the mucosa layer L and the serosa Q closer to each other so as to narrow the space (for example, the tissue space) in the submucosal layer N.

Once the spreading blocks W1 and W2 are formed, the ethanol Z is injected into the submucosal layer N in the target region R (supplying step S4) so as to damage the mucosa basal layer M in the target region R, as illustrated in FIG. 23. Then, by using the constrictive effect of the tissue around the target region R undergoing the process of forming scars as the damaged tissue heals, a part of the region extending from the vicinity (lower part of the esophagus) of the gastroesophageal junction H to the cardiac part J is constricted.

As described above, in this embodiment, the tissues in the submucosal layer N tucked by suturing function as the spreading blocks W1 and W2. Moreover, unlike in the case of forming the spreading blocks W1 and W2 by using an spreading inhibitor such as the sodium hyaluronate solution Y, there is no need to consider the combination of the sodium hyaluronate solution Y and a substance that damages the tissue at the position between the mucosa layer L and the muscle layer P in the target region R. Thus, there is no need to pose limits on the type of substance that damages the tissue at the position between the mucosa layer L and the muscle layer P in the target region R.

In the embodiments described above, the spreading blocks W1 and W2 that extend in the longitudinal direction of the gastroesophageal junction H are respectively formed on the both sides of the target region R in the circumferential direction of the gastroesophageal junction H; however, any approach, with which the spreading blocks W1 and W2 can prevent the substance, such as ethanol, injected into the target region R from spreading beyond what is necessary in the circumferential direction of the gastroesophageal junction H, will suffice. For example, the spreading blocks W1 and W2 may be formed to extend diagonally with respect to the longitudinal direction of the gastroesophageal junction H.

Figure 24:
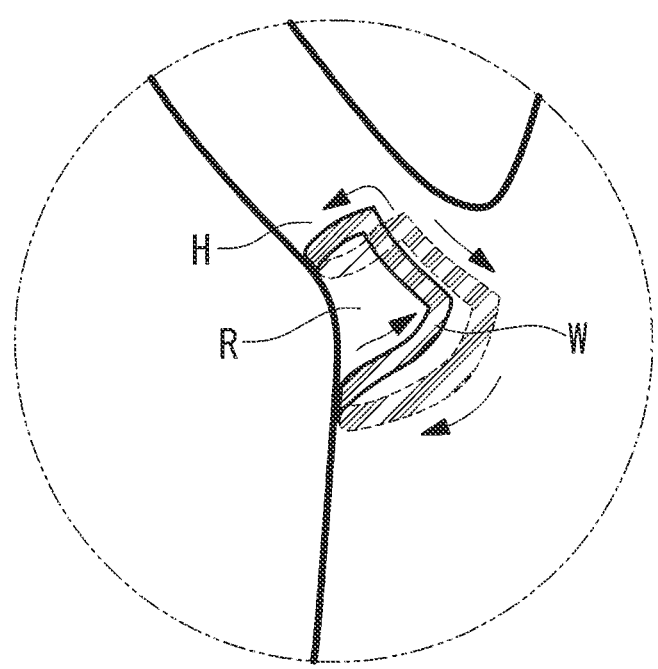
FIG. 24 is a plan view illustrating an example of an spreading block formed around the entire circumference of the target region.

Alternatively, for example, as illustrated in FIG. 24, spreading blocks W may be formed around the entire circumference of the border of the target region R. In other words, spreading blocks that extend in a direction orthogonal to the circumferential direction of the gastroesophageal junction H may be formed at the position between the mucosa layer L and the muscle layer P and on the both sides of the target region R in the circumferential direction, and spreading blocks that extend in a direction orthogonal to the longitudinal direction of the gastroesophageal junction H may be formed at the position between the mucosa layer L and the muscle layer P and on the both sides of the target region R in the longitudinal direction so that these spreading blocks surround the target region R.

In this case, for example, as illustrated in FIG. 24, the procedure of the forming step S3 of the first, second, and third embodiments described above may be performed clockwise or anticlockwise along the border of the target region R so as to form the spreading blocks W around the entire circumference of the border of the target region R.

When spreading blocks W are formed around the entire circumference of the border of the target region R, the substance supplied to the target region R can be blocked by the spreading blocks W even when the substance spreads in the longitudinal direction or the circumferential direction of the gastroesophageal junction H, and thus spreading of the substance beyond the target region R can be reliably suppressed.

Although the ethanol Z is injected at the position between the mucosa layer L and the muscle layer P in the target region R by using the treatment tool equipped with an injection needle in the embodiments described above, any approach, with which the tissue at the position between the mucosa layer L and the muscle layer P in the target region R can be damaged by a substance such as ethanol Z, will suffice. For example, a substance, such as ethanol Z, may be sprayed or applied to the surface (mucosal surface) of the mucosa layer L in the target region R. In such a case, the ethanol Z penetrates from the mucosal surface and damages the mucosa basal layer M from the mucosal surface side of the mucosa basal layer M.

Although embodiments of the present invention are described in detail with reference to the drawings in the description above, the specific structures are not limited to these embodiments and include design modifications etc., within the scope of the present invention. For example, the present invention is not limited to implementations in the embodiments and modifications described above but may be applied to embodiments in which these embodiments and modifications are appropriately combined, without specific limitation.

Although in the embodiments described above, the case in which the gastrointestinal tract constricting method is applied to the treatment of gastroesophageal reflux disease is described, any approach, with which the substance is supplied to the target region R of the gastrointestinal tract and the gastrointestinal tract can be constricted by using the constrictive effect of the tissue around the target region R undergoing formation of scars as the damaged tissue heals, will suffice. Thus, the application range is not limited to the therapy of the gastroesophageal reflux disease, and the site where the method is to be applied is not limited to the gastroesophageal junction H.

The following invention is derived from the embodiments described above.

An aspect of the present invention provides a method for constricting a gastrointestinal tract, comprising forming spreading blocks while observing a gastrointestinal tract with an endoscope inserted into the gastrointestinal tract, the spreading blocks being formed at a position between a mucosa layer and a muscle layer and on both sides of a target region, which is to be damaged by a substance, in a circumferential direction of the gastrointestinal tract so that the spreading blocks block spreading of the substance in the circumferential direction of the gastrointestinal tract to prevent spreading of the substance to an outer side of the target region, and supplying the substance to a mucosal surface of the target region or to the position between the mucosa layer and the muscle layer after formation of the spreading blocks.

According to this aspect, the gastrointestinal tract can be constricted by supplying a substance at a position between the mucosal surface or mucosa layer and the muscle layer in the target region of the gastrointestinal tract so as to damage the tissue thereat and by utilizing the constrictive effect of the tissue around the target region undergoing the process of forming scars as the damaged tissue heals.

In this case, since the tissue at the position between the mucosa layer L and the muscle layer P of the target region R is damaged by the substance, the invasiveness is low and the procedure is simple compared to the case in which the tissue is damaged by incision of the gastrointestinal tract or removal of the tissue in the gastrointestinal tract. Moreover, since the spreading blocks are formed at the position between the mucosa layer and the muscle layer and on the both sides of the target region in the circumferential direction of the gastrointestinal tract prior to the supply of the substance, the substance supplied to the target region is blocked by the spreading blocks and is prevented from spreading beyond what is necessary in the circumferential direction of the gastrointestinal tract, and excessive constriction of the gastrointestinal tract can be prevented. Thus, the gastrointestinal tract can be constricted by making the desired region of the gastrointestinal tract contract by a simple and low-invasive procedure.

In the aspect described above, the spreading blocks may include a first spreading block formed at a position between the mucosa layer and the muscle layer in a region adjacent to one end of the target region in the circumferential direction of the gastrointestinal tract, and a second spreading block formed at a position between the mucosa layer and the muscle layer in a region adjacent to the other end of the target region in the circumferential direction of the gastrointestinal tract, the second spreading block being formed after the first spreading block.

According to this feature, separate spreading blocks are formed on the both sides of the target region in the circumferential direction of the gastrointestinal tract, and thus the spreading blocks can be easily and highly accurately formed.

In the aspect described above, the spreading blocks may include a first spreading block formed at a position between the mucosa layer and the muscle layer in a region adjacent to one end of the target region in the circumferential direction of the gastrointestinal tract so as to extend along a longitudinal axis of the gastrointestinal tract, and a second spreading block formed at a position between the mucosa layer and the muscle layer in a region adjacent to the other end of the target region in the circumferential direction of the gastrointestinal tract so as to extend in the longitudinal axis of the gastrointestinal tract, the second spreading block being formed after the first spreading block.

According to this feature, the spreading blocks that extend along the longitudinal axis of the gastrointestinal tract are easily and highly accurately formed on the both sides of the target region in the circumferential direction of the gastrointestinal tract, and these spreading blocks can more effectively prevent the substance supplied to the target region from spreading beyond what is necessary in the circumferential direction of the gastrointestinal tract.

In the aspect described above, the spreading blocks may be formed around the entire circumference of a border of the target region.

According to this feature, spreading of the substance beyond the target region can be reliably suppressed.

In the aspect described above, the spreading blocks may be formed by supplying an spreading inhibitor, which is composed of a liquid having a higher viscosity than the substance, at a position between the mucosa layer and the muscle layer and on the both sides of the target region in the circumferential direction of the gastrointestinal tract.

According to this feature, spreading blocks can be easily formed on the two ends of the target region in the circumferential direction of the gastrointestinal tract by a simple procedure of supplying a liquid at a position between the mucosa layer and the muscle layer of the gastrointestinal tract.

In the aspect described above, the spreading blocks may be formed by cauterizing the submucosal layer on the both sides of the target region in the circumferential direction of the gastrointestinal tract.

According to this feature, spreading blocks can be easily formed on the two ends of the target region in the circumferential direction of the gastrointestinal tract by a simple procedure of cauterizing the submucosal layer of the gastrointestinal tract.

In the aspect described above, the spreading blocks may be formed in the submucosal layer by compressing the submucosal layer on the both sides of the target region in the circumferential direction of the gastrointestinal tract.

According to this feature, damage inflicted on the tissue by formation of the spreading blocks can be suppressed since the method simply involves compressing the submucosal layer.

REFERENCE SIGNS LIST

1 endoscope
H gastroesophageal junction (gastrointestinal tract)
R target region
W spreading block
W1 first spreading block (spreading block)
W2 second spreading block (spreading block)
Y sodium hyaluronate solution (spreading inhibitor)
Z ethanol (substance)

The invention claimed is:

1. A gastrointestinal tract constricting method, comprising:
forming first and second spreading barriers while observing the gastrointestinal tract with an endoscope inserted into the gastrointestinal tract, the first and second spreading barriers being formed at a radial position between a mucosa layer and a muscle layer and in a circumferential position on first and second sides of a target region, which is to be damaged by a substance, the first and second spreading barriers being spaced apart in a circumferential direction of the gastrointestinal tract so that the first and second spreading barriers block spreading of the substance in the circumferential direction of the gastrointestinal tract to prevent spreading of the substance to an outer side of the target region, and
supplying the substance to a mucosal surface of the target region or to the position between the mucosa layer and the muscle layer after formation of the first and second spreading barriers.

2. The gastrointestinal tract constricting method according to claim 1, wherein the first and second spreading barriers include a first spreading block formed at the radial position between the mucosa layer and the muscle layer in a region adjacent to the first side of the target region in the circumferential direction of the gastrointestinal tract, and a second spreading block formed at the radial position between the mucosa layer and the muscle layer in a region adjacent to the second side of the target region in the circumferential direction of the gastrointestinal tract, the second spreading block being formed after the first spreading block.

3. The gastrointestinal tract constricting method according to claim 1, wherein the first and second spreading barriers includes a first spreading block formed at the radial position between the mucosa layer and the muscle layer in a region adjacent to the first side of the target region in the circumferential direction of the gastrointestinal tract so as to extend along a longitudinal axis of the gastrointestinal tract, and a second spreading block formed at the radial position between the mucosa layer and the muscle layer in a region adjacent to the second side of the target region in the circumferential direction of the gastrointestinal tract so as to extend in the longitudinal axis of the gastrointestinal tract, the second spreading block being formed after the first spreading block.

4. The method for constricting a gastrointestinal tract according to claim 1, wherein the first and second spreading barriers are formed by supplying a spreading inhibitor, which is composed of a liquid having a higher viscosity than the substance, at the radial position between the mucosa layer and the muscle layer and in the circumferential position on the first and second sides of the target region in the circumferential direction of the gastrointestinal tract.

5. The method for constricting a gastrointestinal tract according to claim 1, wherein the first and second spreading barriers comprise first and second spreading blocks separately formed and spaced apart from each other in the circumferential direction.

* * * * *